United States Patent [19]

Roberts

[11] 4,455,090

[45] Jun. 19, 1984

[54] APPARATUS FOR MEASURING SURFACE REFLECTANCE CHARACTERISTICS

[75] Inventor: Brian S. Roberts, Gerrards Cross, England

[73] Assignee: The Wiggins Teape Group Limited, Great Britain

[21] Appl. No.: 169,670

[22] Filed: Jul. 17, 1980

[30] Foreign Application Priority Data

Jul. 26, 1979 [GB] United Kingdom ................. 7926129

[51] Int. Cl.³ ........................................... G01N 21/01
[52] U.S. Cl. .................................................. 356/448
[58] Field of Search ........................ 356/448, 319–325, 356/445

[56] References Cited

U.S. PATENT DOCUMENTS 4,373,818  2/1983  Yamamoto et al. ................ 356/408

FOREIGN PATENT DOCUMENTS

| 1072139 | 6/1967 | United Kingdom . |
| 1079999 | 8/1967 | United Kingdom . |
| 1106111 | 3/1968 | United Kingdom . |
| 1298517 | 12/1972 | United Kingdom . |
| 1338464 | 11/1973 | United Kingdom . |
| 1498418 | 2/1974 | United Kingdom . |
| 1367825 | 9/1974 | United Kingdom . |
| 1384501 | 2/1975 | United Kingdom . |
| 1404573 | 9/1975 | United Kingdom . |
| 1444188 | 7/1976 | United Kingdom . |
| 1456541 | 11/1976 | United Kingdom . |
| 1458358 | 12/1976 | United Kingdom . |
| 1530947 | 11/1978 | United Kingdom . |
| 2013334 | 8/1979 | United Kingdom . |
| 1560482 | 2/1980 | United Kingdom . |

Primary Examiner—Bruce Y. Arnold
Attorney, Agent, or Firm—Burns, Doane, Swecker & Mathis

[57] ABSTRACT

An instrument for measuring surface characteristics based on the opacity of a material has an optical projection system for illuminating a sample and photocell arrangement for measuring light reflected from the sample. The instrument contains standard black and white surfaces with reference to which the sample opacity is measured. The photocell signal is digitized and the results processed and calculations made by a microprocessor system enabling sets of results to be stored and mean and standard deviations to be calculated. The instrument is particularly intended for testing paper and, in connection with carbonless copy paper, enables a measure to be made of the density of an imprint relative to the background that is called calender intensity.

18 Claims, 14 Drawing Figures

APPARATUS FOR MEASURING SURFACE REFLECTANCE CHARACTERISTICS

DESCRIPTION

1. Field of the Invention

This invention relates to the measurement of one or more surface characteristics of paper or other material. The invention has application to the measurement of reflectance or to a characteristic based on reflectance.

2. Background of the Invention

It has been the practice to assess certain characteristics of paper by making light reflectance measurements from the surface of the paper. Such measurements may be made and the results calculated manually. This is laborious and time consuming and liable to error.

One measurement that may be made on paper is that of the reflectance of the paper surface as referred to defined standard black and white surfaces. Such reflectance measurements may be referred to generally herein as opacity. The Technical Association of Pulp and Paper Industries (TAPPI) of the United States of America has provided a particular standard by which opacity is measured. Opacity measurements made in accord with this particular standard will be referred to as opacity (TAPPI) to distinguish them from the more general usage of the term.

In the special field of carbonless copy papers, there is a need to make a measurement on these papers by which the effectiveness of the paper to provide a copy can be judged.

With such papers, the back surface of a sheet carrying a coating of microcapsules containing a solution of colour precursors is brought into contact with the front surface of a second sheet carrying a co-reactant for the colour precursors. When a written or typed impression is made on the front of the first sheet, the capsules rupture in the zone underlying the impression to release the colour precursor solution. The colour precursors react with the co-reactant to generate a coloured image on the second sheet corresponding to the configuration of the impression, for example a typed character.

It is desirable to provide a measurement of the visual definition of the character and this can be done by comparing the reflectance of the area containing the colour image with an adjacent area in which no image exists.

A convenient way of making this kind of measurement is to calender a central strip of a carbonless copy paper to provide a coloured strip whose reflectance can be compared with that of an adjacent uncalendered area. This measurement of relative opacity will be referred to herein as calender intensity (C.I.).

SUMMARY OF THE INVENTION

There will be described hereinafter a measuring instrument which enables both general opacity measurements and calender intensity measurements to be made.

The present invention is concerned with providing electronic apparatus for this purpose and, in particular, enables advantage to be taken of a microprocessor in the organizing and running of test routines, the calculation of results and their collation. For convenience, the following description will be confined to making measurements on paper although it will be apparent that similar measurements can be made on other materials.

These will be described hereinafter an instrument embodying the invention which performs two basic measurements and which derives other related results therefrom. The first of these measurements is a general measure of opacity. The main steps of this measurement are to (1) measure the reflectance of a standard black surface;
(2) measure the reflectance of a standard white surface;
(3) measure the reflectance of the paper surface under test;
(4) calculate the reflectance of the paper surface as a percentage using the standard surfaces to define a prescribed scale, e.g. black and white (clean magnesium carbonate) represent 0% and 98% reflectance respectively. As will be explained the white standard may be more conveniently of another more durable material for normal use. This standard can then be checked by reference to the magnesium carbonate standard.

The reflectance is measured in each case by measuring the reflected light intensity from the surface in question when illuminated by light.

The second measurement is a measurement of C.I. in which the main steps are to:

(1) measure the reflectance of a non-impacted area of the paper;
(2) measure the reflectance of an impacted area of the paper;
(3) calculate the impacted area reflectance as a percentage of the non-impacted area, the reflectance of the latter being referred to as background intensity since it represents the background against which a character is read.

Preferably the two reflectances are measured on a prescribed scale, as by initial calibration against standard black and white surfaces. Also the measurement (2) is preferably the mean of a number of measurements at different impacted areas. This averaging technique may also be applied to the background measurement.

The two measurement routines briefly outlined above can be adapted to a measurement procedure which is in accord with TAPPI standards for measuring opacity (TAPPI). This will be discussed later in the more detailed description.

More generally stated, in one aspect the present invention provides apparatus for measuring the opacity of a sample area comprising:

a station for receiving the sample area;

means for generating and directing radiation to said station;

first and second means providing defined standards of reflectance locatable at said station;

photo-sensitive means responsive to radiation reflected from the sample area or a standard located at said station to derive an electrical signal representing the reflected radiation, and a circuit arrangement connected to process the electrical signals representing the sample area and standards, said circuit arrangement being operable to digitize the signals and to compute the reflectance of the sample area with reference to said standards.

In another aspect of the invention there is provided apparatus for measuring the relative opacity of a first sample area with respect to at least one other sample area comprising a station for receiving each of the two areas;

means for directing radiation to said station;

first and second means providing defined standards of reflectance locatable at said station;

photo-sensitive means responsive to radiation reflected from a sample area or standard located at said station to derive an electrical signal representing the reflected radiation;

and a circuit arrangement connected to process the electrical signals representing the sample areas and standards, said circuit arrangement being operable to digitize the signals and to compute the reflectance of the sample areas with reference to said standards and thence to compute the relative reflectance of the first sample area with respect to the other sample area or areas.

The apparatus defined in the preceding two paragraphs is usable to perform measurements of opacity and C.I. according to the methods above-mentioned. It can also be used to provide a measure of opacity (TAPPI).

A measuring apparatus embodying the invention and the methods of using it will now be described in greater detail with reference to the accompanying drawings.

The apparatus of the invention may be conveniently divided into two parts. One is the optical system from which is obtained an electricl signal representing light intensity; the other is an electronic measurement and control circuit based on a microprocessor that is responsive to the light intensity values represented by the just-mentioned electrical signal.

Figure 1:
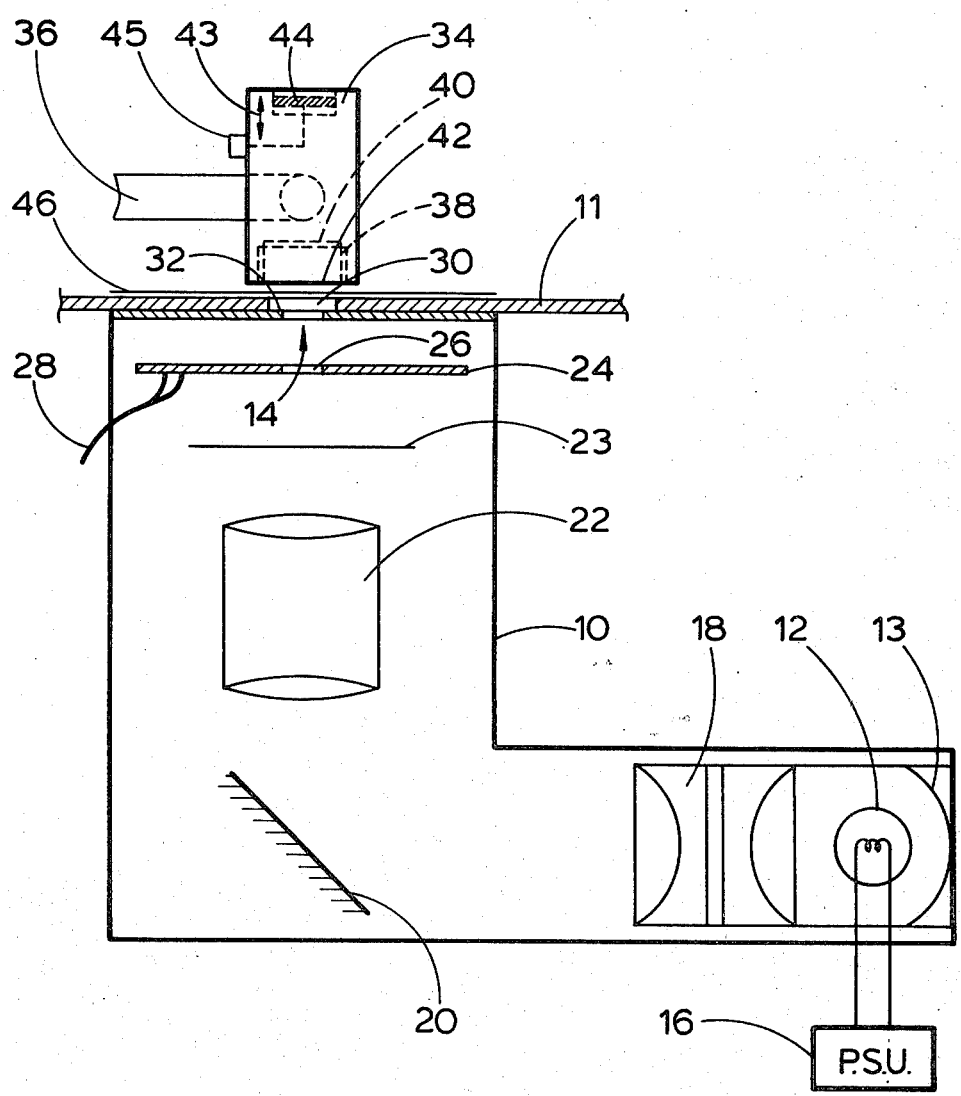
FIG. 1 is a diagrammatic illustration of the optical system of the apparatus and reflectance standards associated therewith.

The optical system will first be described with reference to FIG. 1. The system is contained in a light-tight box 10 of L-shaped section. The light source is a lamp 12 with reflector 13 the light from which is directed through a lens/filter system to a window aperture 14 which is a portion of the top panel 11 of the case of the instrument and which provides a measurement station.

The lamp 12 is rated at 12 volts, 50 watts (Atlas M32) but is under-run by energising it from a stabilised supply 16 operating at, say, 7 volts. In this way the lamp delivers a substantially constant spectrum and has a long life expectancy. The light from the lamp is directed through a condenser lens 18 to a mirror 20 and thence through a projection lens 22 from which a collimated beam of light is projected to the window 14. The use of the mirror 20 enables the optical system to be folded at right-angles and thereby fit more conveniently into the instrument case. A filter 23 is interposed in the collimated light beam to control the spectral characteristic of the light impinging on the window.

Measurements are made of light reflected from a surface superposed on the window 14. The reflected light intensity is measured with the aid of a photocell 24 located between the filter 23 and the window. The photocell has a central aperture 26 that defines the area of the window illuminated by the collimated light. Apertured photocells are available commercially. The one utilised has its central aperture opened out to 13.5 mm. diameter. The aperture of window 14 is coaxial with and has a diameter greater than that in the photocell so that the window is underfilled by the illumination from the photocell aperture. The photocell is of the selenium photovoltaic kind, producing an output on line 28 whose utilisation is discussed below.

In the present case, the characteristics to be measured are those as seen by the eye. Thus the filter 23 is selected in conjunction with the source and photocell to have an overall response equivalent to that of the eye. A suitable filter has been found to be a Kodak No. 102.

The optical system described is not entirely in accord with TAPPI standards for opacity measurement. However, its performance has been found satisfactory and the system can be realised in compact form. It could be substituted by an optical system meeting TAPPI requirements.

The light-tight box is closed to keep dust, etc. out of the optical system and to this end the window aperture 14 is closed by an optically-transparent window element 30. While glass or clear plastics material might be used, it is preferred to use as the window element a disc of sapphire. Sapphire is hard and resistant to abrasion; it is clear and has stable spectral characteristics from the ultraviolet to infrared; and it does not interfere with measurements taken over the visible portion of the spectrum. Even with the use of sapphire there is a window effect which modifies the measurement. This effect is compensated for in a manner discussed hereinafter. Sapphire discs are obtainable commercially and the one employed is 16 mm. in diameter by 1 mm. in thickness. The disc is seated on a ledge 32 in the top 11 of the light box, so that the actual window diameter is less than that of the element 30. It is thus the inside diameter of the ledge which defines the aperture of window 14 discussed above. The ledge has a depth from the top surface equal to the disc thickness so that the disc is seated level with the top surface.

The instrument is also provided with means for calibrating the instrument using black and white standards of known reflectance. To this end a holder 34, for example made of plastics material, is mounted at one end of arm 36, the other end of which is pivotally mounted to the case to have some freedom for both horizontal and vertical movement. The holder is mounted to pivot about the arm axis so that standards set into opposite sides of the holder can be set over the window 14.

The black standard is made from a hollow aluminium cylinder 38 capped at one end 40. The cylinder is set into one face of the holder to have its open end 42 outward and of larger diameter than the window element. The interior surface is micro-sand blasted and black anodised. The open end seats about the window in a light-tight fashion and its reflectance is taken to be zero (0%).

The white standard 44 is a tile of a pigmented glass, and specifically a white vitrolite, which is first cemented into a metal holder and the latter let into a recess in the face of the holder opposite to that containing the black standard. The tile holder is mounted to be movable to and fro in the recess with respect to the face of the holder 34 as indicated by arrow 43. The tile holder is provided with a locking device 45 that is coupled to the holder for the tile 44 as shown diagrammatically in the figure. The tile position is adjusted to provide a reflectance of 78%. The absolute reflectance of a vitrolite tile is greater than this but its apparent reflectance is changed by varying its position on the optical axis. An absolute standard of calibration is achieved with a compacted and clean block of magnesium carbonate which has a reflectance of 98%. The block is placed directly over the window and the instrument adjusted to read 98.0% reflectance. The block is then replaced by the vitrolite tile which is adjusted in position to read 78%. The tile is an easier material to use in practical measurements.

In calibration, the desired standard is seated over the window. For measurement purposes the appropriate area of a paper sample 46 is located over the window and the holder 38 can then serve to hold the sample against the window. The collimated light uniformly illuminates the sample or standard located at the window and the light scattered back through the window is collected over a wide angle by the annular photocell.

Figure 2:
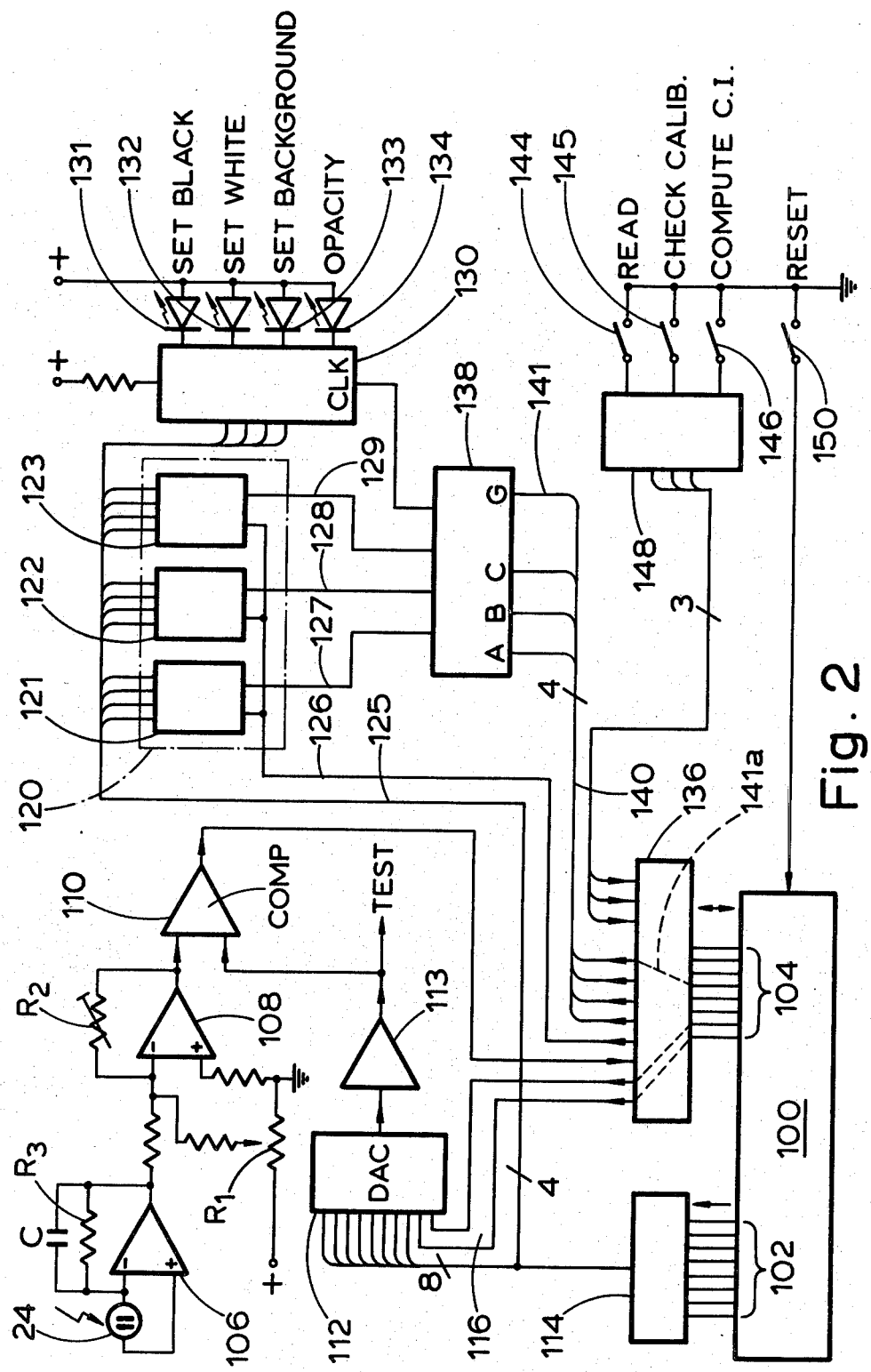
FIG. 2 is a block circuit diagram of the electronic circuitry of the apparatus including a microprocessor system.

The instrument is controlled by a microprocessor system, the block diagram of which is shown in FIG. 2. It should be noted at this point that the instrument described has been developed around the Fairchild F8 CPU device which is an 8-bit device. Many other devices are available. Specific circuit arrangements and programs for these various devices are within the compass of those skilled in the art.

Referring to FIG. 2, the microprocessor 100 has two 8-bit ports 102 and 104. Both ports are bidirectional in operation. In the circuit shown the port 102 carries alphanumeric information in hexadecimal code and this information is output only. The port 104 is mainly concerned with control signals and both sends and receives such signals. It also receives certain measurement data, as will be described. The reflectance signals derived from the photocell 24 in FIG. 1 are analog and it is necessary to first digitise the signals for handling by the microprocessor.

The output voltage of the photocell 24 is applied to the input of an operational amplifier 106, the feedback network of which includes resistor $R_3$ in parallel with a capacitor C. The applied feedback causes the stage to operate with a virtual earth input, i.e. very low input impedance, so that the photocell 24 is working into a near short circuit. The amplifier circuit acts as a current-to-voltage converter producing an output voltage proportional to input current. It is found that the photocell short circuit current has a good linearity with respect to impinging light intensity. Thus the output voltage of stage 106 is a linear function of light intensity. The capacitor C provides some low pass filtering, but better filtering is obtained by a technique described below. The output voltage of the first amplifier 106 is applied to a second operational amplifier stage 108 including adjustable resistors $R_1$ and $R_2$ for setting the stage output voltage corresponding to black and white respectively. The setting of the black and white limits is not critical because the microprocessor takes the values read for black and white (white vitrolite standard) and treats them as 0% and 78% reflectance respectively. By way of example the voltage readings obtained may be as follows with the reflectance in percent in brackets.

MgCO$_3$ block: 9.90 (98.0)
Black standard: 0.10 (0.0)
Vitrolite tile: 7.30 (78.0) The apparent discrepancy between the voltage reading of the vitrolite tile and the percentage reflectance is due to the window effect at the sapphire window 30. The voltage readings obtained are converted into apparent reflectance percentages by operating according to a linear curve of reflectance versus voltage whose constants are set by the voltage readings for the carbonate block and the Black standard. The apparent reflectance readings are entered into a look-up table from which the true reflectance is obtained. The table may be operated in suitable increments of say 1% or of 0.5% for better accuracy. The look-up table and its realization is discussed further hereinafter.

The output voltage of stage 108 is set slightly above zero for the black standard to ensure a negative voltage or zero is never obtained. To convert the output voltages to digital values the output of stage 108 is applied to one input of a comparator 110 whose second input is fed with the output of a digital-to-analog converter (DAC) 112 taken via a buffer amplifier 113. The DAC is based on an AD 7520 device having a 10-bit input. The buffer amplifier uses a type AD 518 device. Apart from feeding the comparator, the amplifier output provides a useful test point for checking the correctness of the analog-to-digital conversion process.

The analog-to-digital conversion performed with the aid of the DAC112 uses all ten bits of the device input. The eight most-significant bits of the converter input are connected to respective outputs of the port 102 of the microprocessor 100 via respective buffer gates shown together simply as a buffer stage 114. The two least significant bit inputs are activated through two outputs of port 104 taken over lines 116 via buffer gates in a unit 136. The two port outputs are used exclusively for this purpose as indicated by the dashed line connections.

The comparator output is taken to one terminal of the bidirectionally used ports through a gate in unit 136. When a conversion operation is required the microprocessor controls a gate in unit 136 to allow the comparator output to be applied to the port terminal and with the aid of the comparator, the microprocessor adjusts the binary values on the 10-bit DAC input using a successive approximation procedure starting from the most significant bit. Such procedures are well known and will not be described further. At each completed conversion the final digital value set up in the microprocessor can be stored, if required.

The speed of conversion is such that for each measurement the conversion procedure can be repeated numerous times whereby a high order of filtering is obtained. In the instrument in question, each measurement made is performed by summing one hundred and twenty eight successive conversions and dividing by that number. As each conversion only takes about 0.3 ms, a completed measurement is performed very rapidly. It has been found that this averaging is highly effective in filtering out noise, hum etc. that may be superimposed on the wanted photocell signal.

The DAC 112 operates continuously but, as will be explained hereinafter, four outputs of the port 102 are shared for other data transmission. During periods when such other data is being sent, although the DAC is still operative, its output cannot be considered as valid. The microprocessor 100 is organised to ignore the output of comparator 110 during these periods by disabling the relevant gate in unit 136.

The value of each measured reflectance is displayed as a percentage on a display unit 120 mounted at the top panel of the instrument to be readily seen by the operator. A three-digit display comprising individual display units 121, 122, 123 is used enabling percentages from 00.0 to 99.9 to be displayed in decimal form. The units 121 and 122 provide hexadecimal displays which allow code letters to be displayed and also for purposes discussed below. The third digital unit 123 need only provide a numerical display with decimal point. The units 121 and 122 may be Hewlett-Packard type 7340 while the unit 123 is type 7302. These particular units are self-latching, that is, once data is entered on its inputs, a unit continues to display the data after removal of the input data until fresh data is entered. This facility is taken advantage of by sending input data to the display units over a common data bus 125 and activating the units sequentially to display a complete number.

Four parallel input lines are required for each display unit. As seen in FIG. 2, the bus comprises four lines from output port 102 taken via buffer stage 114, these lines being shared with the DAC 112. When a display operation is required the microprocessor 100 applies the successive items of 4-bit hexadecimal data representing the numbers or letters to be displayed while at the same time selecting the display unit which is to receive each item of data. The selection is done through the control port 104. Each display unit has two control inputs. A first input is connected in parallel with the corresponding control inputs of the other units to line 126. A high level applied to this line holds the displays blank. A low level activates the displays including inserting the decimal point in the last digit display 123. A second input of each device is separately controlled over lines 127, 128 and 129 respectively to activate the device to receive data for entry into the latch. The data bus is also connected to the respective inputs of a 4-bit latch 130. This is a device containing four D-type latches having their respective D-inputs connected to respective ones of the four data lines and having their respective $\bar{Q}$ outputs connected to energise respective light-emitting diodes (LEDs) 131–134. The diodes are mounted at the top panel of the instrument case to provide instructions to the operator as the microprocessor proceeds through a routine. The LEDs are associated with the legends "SET BLACK", "SET WHITE", "SET BACKGROUND" and "OPACITY". The significance of these instructions will become clearer in the later description.

Only one instruction is required at a time so that the corresponding one of the four lines of bus 125 has a high level applied to it and at the same time a low level is applied to the common clock input (CLK) of latch device 130 to set the selected latch. Upon removal of the clock input signal, the selected LED remains activated by the D-type latch that was set.

Thus far, exercise of a number of control functions has been described. These are effected via the port 104 of the microprocessor which, it will be recalled, has an 8-bit capability and is bidirectional. Some further discussion of both the output and input functions of the microprocessor will now be given.

The microprocessor port couples with the input and output lines through a controllable gate system shown as unit 136. This unit comprises buffer gates for incoming and outgoing signals which are controlled by port 104. The sequence of operation of the gates is under the control of the microprocessor program. The design of a particular system is within the compass of those skilled in the art and will not be described in detail. In the illustrated embodiment the gate system 136 includes the respective buffer gates for lines 116 leading to the DAC; and, it routes control signals to the blanking inputs of display 120 over line 126, to the other control inputs of the display, and the latch device 130 through a unit 138.

The unit 138 is a 4–16 line decoder, e.g. a type 74154 device, having four inputs connected via four lines, together denoted 140, to receive control signals from the microprocessor. The device 138 denotes the control signal to select one of sixteen output terminals, only four of which are used in the present case. The device has four select inputs (only three of which are used) and two strobe inputs, one of which (not shown) is held permanently low and the other of which (denoted 141) is used as a general control of unit 138, selection only being possible when the strobe input is low. This strobe input is controlled by an output of port 104 reserved solely for this purpose as indicated by dash line connection 141a. The connection includes a buffer gate. The other three inputs (A,B,C) are used for selecting the required one of four output lines in accordance with a 3-bit select signal. Three output lines are the lines 127–129 that control the individual display units and a further line is connected to the clock input CLK of latch 130.

Turning now to the control inputs to the microprocessor port 104, there are four. One is over a line from the comparator 110. The other three are from a set of switches 144, 145, 146 mounted on the top panel of the instrument case. Conveniently, these are push-button switches or capacitive touch switches. These four input lines are gated to four of the terminals of port 104 whch are bidirectionally employed. The switches 144–146 are connected to the unit 136 through a priority encoder (type 74148) 148. Upon actuating one of the switches the encoder applies signals to the associated three-state gate in unit 136. The priority encoder ensures that, should more than one switch be pressed, the switches 144, 145 and 146 have priority in that order. The priority encoder could be omitted and replaced by a priority routine within the microprocessor.

The switch 144 is associated with the READ function already mentioned. Its actuation causes a reading to be entered from the photocell 24. Switch 145 is associated with a CHECK CALIBRATION function and sets the microprocessor into a routine to check calibration as will be subsequently described. Switch 146 is pressed for COMPUTE C.I. where the instrument is set up for measuring calender intensity. This is also further described below.

The microprocessor 100 has one further input. This is from a RESET switch 150 which may be a push-button switch or a capacitive tough switch mounted on the top panel of the instrument and which is taken to a separate input of the microprocessor. Activation of this switch sets the microprocessor to a start-up condition in its program.

It will have been noted that the four lines of bus 125 share four outputs of the microprocessor port 102 with the DAC input which requires all eight outputs of the port. The control system described and exercised through port 104 enables this sharing to take place without interference. When a digital-to-analog conversion is taking place all the lines 126–129 and the clock input CLK of latch device 130 are held high so that these devices are not responsive to signals on their input lines. When these devices are being activated to display data or instructions, the DAC 112 is operative but, as already discussed, its output is not valid and the comparator output is ignored.

The general organisation of the microprocessor 100 will now be described. It will be realised by those skilled in the microprocessor art that specific details depend on the particular microprocessor device chosen and which vary in how much can be done "on chip" and thus as to what ancillary devices are required. The illustrated microprocessor is designed around the Fairchild F8 family of devices. Similarly, the working out of the detailed programs is within the compass of those skilled in the art given the particular device that they have to work with. Following a description of the microprocessor with reference to FIG. 3, there will be given a description of the basic steps in the various routines in which the instrument is operable.

Figure 3:
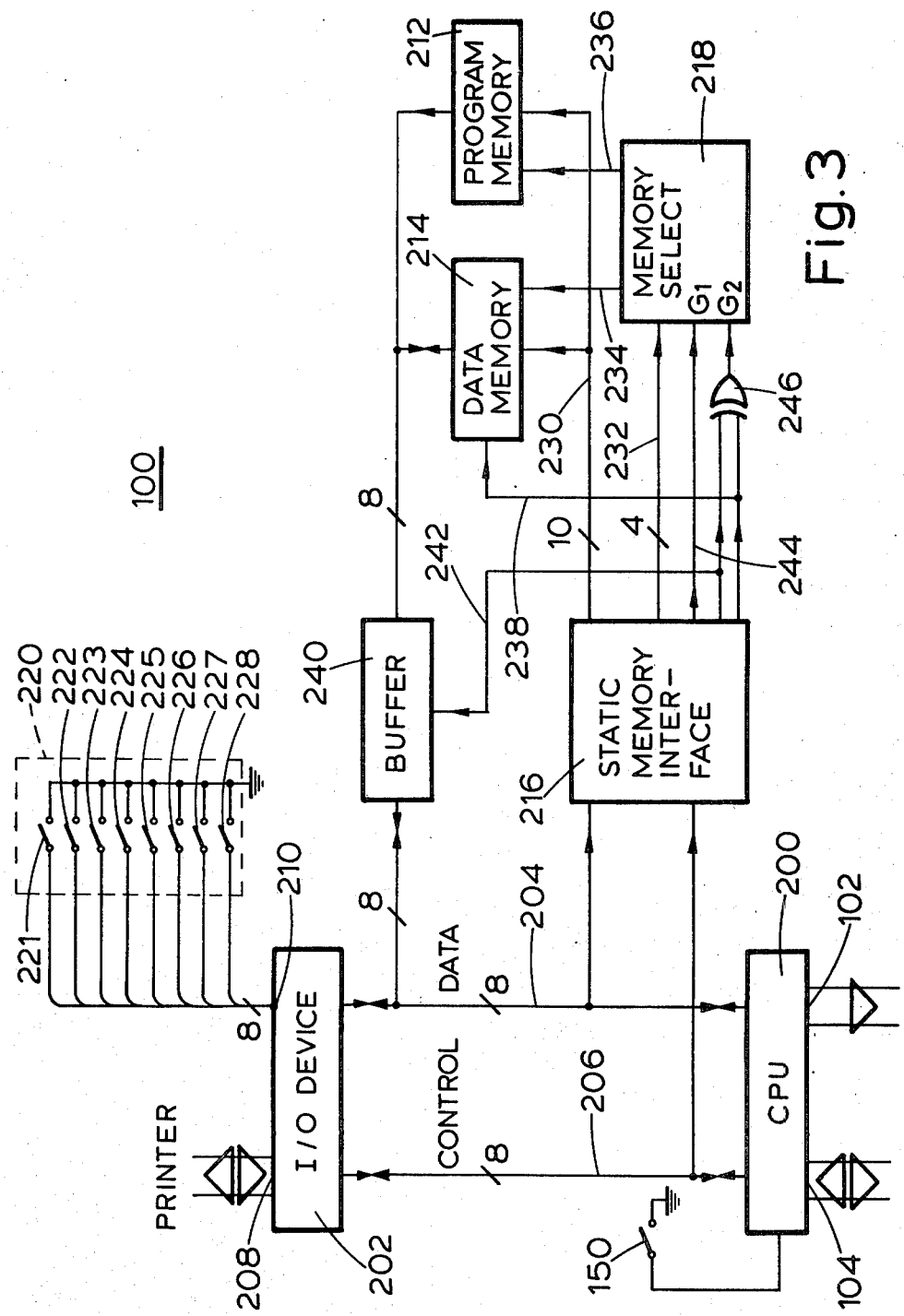
FIG. 3 is a block diagram showing elements of the microprocessor system in greater detail.

Referring to FIG. 3, the heart of the microprocessor is a central processor unit (CPU) 200 which is the F8 device type 3850. This device has the bidirectional ports 102, 104 seen in FIG. 2.

Associated with the CPU 200 is an F8 peripheral input/output (I/O) device type 3861. This device is denoted 202 and is connected to the CPU via an 8-bit data bus 204 and an 8-bit control bus 206. The I/O device 202 has two ports 208 and 210. The port 208 is a data output port to which a printer may be connected directly. Alternatively or in addition the data output appearing at port 208 can be sent to a teleprinter via an appropriate driver unit.

The other port 210 of the I/O device provides an input for a group of switches collectively denoted 220. These switches and their functions are set out in greater detail later. The already mentioned reset switch 150 (FIG. 2) is connected directly to the external reset terminal (pin 37) of the CPU 200. Actuation of this switch causes the microprocessor to stop and, after release of the switch, to go to the first step of the program.

The instrument can be provided with an interface unit in accordance with the IEEE 488 (1975) standard which relates to an instrumentation communication protocol. Such a unit is connected to the data and control buses 204 and 206. The design is not relevant to an understanding of the present invention.

The CPU 200 is used in conjunction with a program memory 212 and a data memory 214. The program memory comprises a number of devices type 2708, which are 8-bit EPROMS (electrically programmable, ultra-violet erasable read-only memory devices), each having a capacity of 1024 bytes (1 Kbyte). They are addressed in a manner to be described.

The memory 212 is also used to store the look-up table mentioned earlier. Assuming that readings to 0.5% are required, each apparent reflectance percentage calculated is effectively rounded to a nearest half percent increment. With each incremental value, there is associated an address in memory 212 and at that address will be found the corrected value that incorporates the compensation for the window effect. The effect, whose physical origins are not clear, can be determined experimentally for a sample instrument with a window of given material and dimensions. Each individual instrument is then checked to ensure it is within specification. The erasable type of memory device allows individual calibration of a particular instrument, if desired.

The data memory 214 is used for storing, for example, reflected light intensity data read into the microprocessor with the aid of DAC 112 (FIG. 2). It is also used to store return addresses when sub-routines are executed.

The CPU 200 itself contains 64 bytes of so-called scratch-pad memory which may provide sufficient data storage in some simpler versions of the instrument. The memory 214 uses 2114 type RAM (random address memory) devices, each having a capacity of 1024 bytes of 4-bits each. The devices are connected in pairs to give a capacity of 1 Kbyte of 8-bits for each pair. The data memory is also addressed in a manner to be described.

To address the memories 212 and 214, the control and data buses 204, 206 of the CPU are coupled thereto via a static memory interface device 216 with which is associated a memory select device 218. The device 216 is an F8 family device, type 3853, and the device 218 is a type 74154 4-to-16 line decoder. Device 216 has a 16-line address output. Ten bits from the device 216 are taken on a memory address bus 230 to each of the two memories. In fact all the individual memory devices in both memories have their respective 10-bit address inputs connected in parallel onto bus 230. Another four address lines from device 216 constitute a memory sheet bus 232 and are connected to the 4-bit input of device 218 from which emanates a first eight-line select bus 234, each line of which is taken to the enable input (pin 20) of a respective one of eight devices constituting program memory 212, and a second eight-line select bus 236, each line of which is carried to the parallel-connected enable inputs of a respective pair of memory devices constituting the data memory 214.

The addressing of the data memory may be for reading-out writing-in data. Each of the constituent devices has a write/read input which is connected by line 238 to a "RAM write" output (pin 6) of the interface device and which is controlled by the static memory interface 216. The binary state of line 238 determines the read or write condition of the data memory.

Each memory 212 and 214 provides an 8-bit output and these are connected in parallel to and applied through a bidirectional buffer 240 to the data bus 204 of the CPU. The program memory only sends program instructions to the CPU. They are also applied to the interface device 216 enabling the program to be incremented as required (the specified device incorporates a program counter). The data memory both sends data to the CPU and receives data from it. Hence there is a the need for a bidirectional buffer. The buffer comprises two inverse-parallel connected stages, each stage comprising a pair of 4-bit buffer devices (type 340097) connected in parallel. The direction of transmission is controlled by the state of a binary signal on line 242 connected to a "CPU read" output (pin 34) of the interface device 216 controlled by CPU 200. The stages are interconnected by an inverter (not shown) such that the binary state of the line 242 determines which stage is enabled for transmission.

The two remaining address outputs from static memory interface 216 are "ORed" together (not shown) and the resultant line 244 used to disable or enable memory select device 218 via G1. Also the "RAM write" output 238, and CPU read line 242 are connected via an exclusive-or gate to G2 of memory-select device 218. The memory-select device is enabled only when its input G2 is at logic 0 (low), that is only when "CPU READ" and "RAM WRITE" are both high or both low.

The operation and control of the memories is as follows, it being remembered that each memory 212 and 214 effectively comprises eight storage devices, each having 1024 addressable storage locations. Consequently a 10-bit address input is required to select one of the 1024 locations in each device.

At a given step in the operation, a 10-bit address is placed on bus 230 via interface device 216. It is firstly necessary to ensure that the memory wanted for this step is selected. This is effected by a 4-bit address on bus 232. The sixteen possible addresses selectable by the four bits are divided into two groups of eight allotted to the respective memories. Thus, the address selects the memory, and by designating the appropriate line on 8-line bus 234 or 236, the device 218 causes not only the memory to be selected but also the appropriate one of the eight storage devices in that memory. In this manner, the address on bus 230 is applied only to the required storage device. In other words, the combined address bits on buses 230 and 232 determine the specific storage location required.

If a storage device in the program memory is addressed, the CPU conditions line 242 to allow the 8-bit word from the addressed storage location to be transmitted to data bus through buffer stage 240. If the data memory 214 is addressed, it may be for the purpose of writing data in or reading data out. Whichever is wanted requires two further steps. One is to condition line 238 for a read or write operation. Secondly, to condition line 242 for data flow to, or from, bus 204 in dependence on whether a read or write operation respectively is required.

To ensure the correct sequence and timing of operations, the memory select device 218 is controlled by the static memory interface 216. This is done via the two lines connected to the gate which includes an EXCLUSIVE-OR function performed on the signals on lines 238 and 242 such that the memory select device is only operative when the "CPU READ" and "RAM WRITE" outputs from the interface device indicate either that the data memory is to place data on the data bus and data is to be read from the memory, or that the CPU is to place data on the data bus and data is to be written into the data memory. The first of these conditions is also observed when an instruction is to be read from the program memory.

To complete this description of the general organization of the microprocessor 100, reference is made to the group of control switches 220 connected to the port 210 of the interface device 202. Switch 221 is an override control switch which needs to be ON (closed) for the other switches to be effective. Switch 222 puts the microprocessor into the opacity measuring condition when ON and into the calender intensity measuring condition when OFF. Switch 223 selects printer when ON. Switch 224 selects teleprinter when ON. Switch 225 selects IEEE488 interface for outputting results when ON. Switch 226 selects opacity resolution to 0.5% when ON and to 1% when OFF. Switch 127 selects mean background mode, this enables a number of measurements to be made, and the mean to be acquired for the background material when measuring CI as is explained hereinafter. Switch 228 selects an electronic test routine when ON. Under this condition the other switches select test functions. Further description of this is not necessary for an understanding of the present invention and will thus not be given.

Having described the optical system and the microprocessor-controlled circuitry of the apparatus, a description will now be given of the use of the instrument to make opacity and calender intensity measurements as well as the manner in which the instrument calibration is established. The instrument performs in a number of routines which are themselves controlled by the stored program. The routines are performed with the aid of instructions entered into the instrument by means of the operator-actuated switches 144–146 and 150 of FIG. 2 and the instrument in turn instructs the operator by means of the legended indicator lights 131 to 134 and the hexadecimal display 120, in particular display units 121, 122. The alpha characters of the hexadecimal code are used to provide information to the operator in accord with the following coding table:

AA: black level low
AB: white level high
BB: calibration error re-calibrate
CA: calibration correct
CC: reset complete
DD: no more measurements—compute C.I. or reset
EE: insufficient data to compute C.I.
FF: operator error The foregoing codings are, of course, in addition to the numerical data displayed by the instrument when performing measurements. The codings are indicators of error conditions. The operator error coding FF is displayed when either the correct calibration sequence is not followed or for opacity values which are negative or greater than 99.9% which will usually mean that the instrument is in need of adjustment.

The switches 144–146 and 150, which are preferably of the push-button capacitive type, the indicators 131–134 and the display 120 are all mounted on the top panel 11 (FIG. 1) of the instrument that also carries the optical head. The switches and indicators are accompanied by the legends marked. The above coding table is also inscribed on the top panel for the benefit of the operator.

Mention has already been made of the switch unit 220 (FIG. 3) whose switches also provide instructions to the instrument. The switches are of a pre-set nature and can thus be located accessibly within the instrument casing. At any one time the described instrument will be set by the condition of switch 222 for measuring opacity or for computing calender intensity as already outlined at the opening of this specification. The condition of switch 222 controls the computation routine performed in response to the pressing of the COMPUTE C.I. button. Before going further into the instrument routines the measurements made will be further discussed. Even if the instrument is set up for computing calender intensity, it is, nonetheless, making opacity measurements to provide the data for computation so opacity measurement will be dealt with first.

Opacity in the present context is the measurement of the reflectance of the surface of a material, which for the present purposes is assumed to be paper. It is not a measurement of light transmittance.

To measure opacity the microprocessor establishes a linear curve $y = mx + c$, where x is the measured reflected light received by the photocell 24 and y is the opacity expressed as a percentage reflectance. The constants m and c can be established in the usual way by establishing two known points on the curve with the aid of the black and white standards contained in the standard holder 34 of FIG. 1, though as will be described below, the constants as such do not need to be calculated.

The black standard is applied to the window aperture 14 and the resulting digital voltage achieved in the microprocessor with the aid of the DAC 112 (FIG. 2) is taken as the value for x and stored, with y assumed to be zero. As stated above, x for black is typically 0.10 volts. The white standard is now applied to the window 14 and the voltage achieved taken as the value for x and stored, with y assumed to be 72%. This is less than the 78% reflectance assumed for the white standard, the vitrolite tile. The discrepancy is due to the window effect whose correction is described below.

Figure 4:
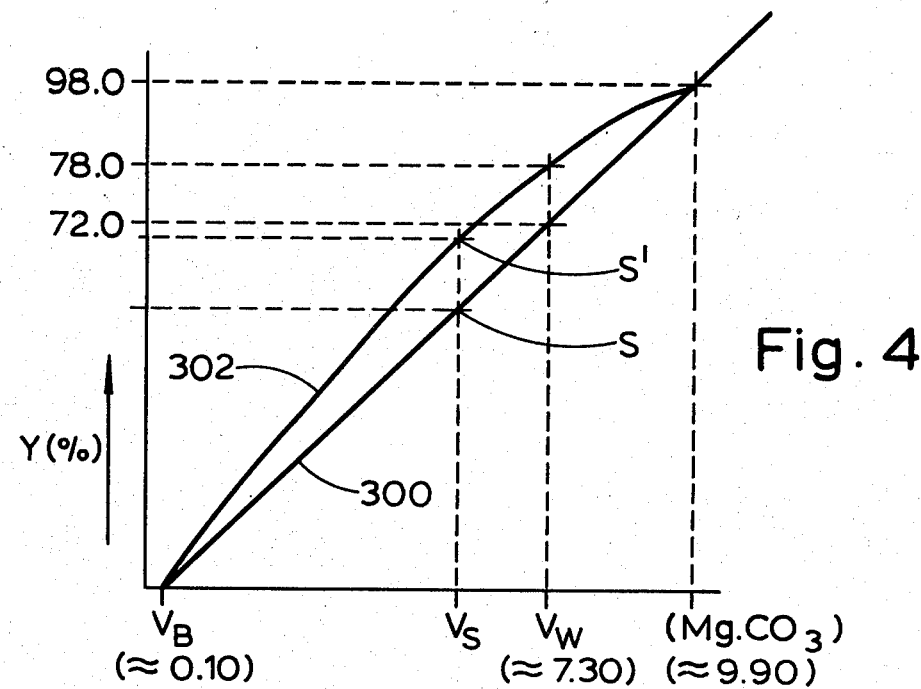
FIG. 4 is a graphical representation to illustrate a correction procedure performed by the microprocessor system.

The microprocessor can now establish the straight line $y = mx + c$ which is shown as line 300 in FIG. 4. In practice the constants of the equation are not computed. Other values can be obtained by applying proportionality based on the black and white standard values which are held in the microprocessor. When a sample is placed over the window it reads somewhere between the black and white values (in theory at least it may be above the vitrolite tile white level), say at point S in FIG. 4 giving a corresponding apparent reflectance. This value is calculated by proportionality and is entered in a storage register in the data memory 214 but is not displayed until a correction has been made for the window effect. It includes losses in the window material, which are substantially uniform over the visible spectrum, plus reflection effects, including multiple reflections, at the window surfaces and sides. The effect is not fully understood and investigation has shown them to be non-linear with respect to measured reflectance. However, they have been found to be consistent for windows of given material and size so that a proper correction can be made.

Thus while the line 300 represents apparent reflectance, the true reflectance is represented by the curve 302 illustrating the non-linearity of the deviation between true and apparent reflectance. The correction of the apparent reflectance is done with the aid of the look-up table included in the program memory 212 as already mentioned. Effectively an apparent reflectance value rounded to the nearest half percent is entered in the table, e.g. a value S in FIG. 4 and the correct value S' read out. For the standard vitrolite tile when the value 72.0 is entered, the corrected value 78.0 is obtained. It is the corrected value that appears as a percentage on the display 120.

It will be recalled that the position along the optical path of the vitrolite tile is adjustable. The locking means 45 is constructed so as to be not adjustable by the operator. The adjustment is made on an initial setting up of the instrument for which purpose the aforementioned clean magnesium carbonate block is used as an absolute standard having a reflectance of 98.0%. In setting up the instrument, the microprocessor is operated in one of its test modes (switch 228 operated). The particular mode allows the microprocessor to digitise the photocell signal with the aid of DAC 112, and directly indicate the value on display 120. In this mode there is no modification or window correction of the digitised signal. The black standard is placed over the window 14 and microprocessor instructed by pressing READ button 144 to digitise and display the value. Resistor R1 is adjusted until the display 120 indicates a value of 01.0. After this a clean block of magnesium carbonate is placed over the viewing window 14, the READ button again actuated, and resistor R2 adjusted so that the display 120 indicates 99.0. The procedures of measuring black and then magnesium carbonate has to be repeated until the values of 01.0 and 99.0 can be obtained without adjustment of either R1 or R2. The vitrolite tile is now placed over the viewing window 14, and its position adjusted to enable a value of 73.0 to be indicated on display 120. This method of calibration is preferred as it eliminates analog offset values. Alternatively the calibration procedure may be made by measuring the output from amplifier 108, and adjusting the resistors to give voltages of 0.1 and 9.9 for black and magnesium carbonate respectively. The tile would be positioned to give 7.3 volts. These voltages are arbitrary, the only requirements being that proportionality is maintained and the DAC 112/113 conversion limits are not exceeded. It will be noted that the calibration difference of 98.0 between the carbonate (99.0) and black (0.10) is the percentage reflectance for the carbonate block. The tile gives an uncorrected reflectance of 72.0%. In subsequent measurement procedures, the black offset (0.10) is deducted before correction is made. This is illustrated in FIG. 4 where the corrected and uncorrected curves are chosen to coincide at the points corresponding to the absolute black and white standards of 0.00 and 98.0%. The instrument is then ready for use and normally is checked for calibration by the standards in the standard holder. Within limits drift in the analogue circuitry connected to the photocell 24 is automatically taken into account by the microprocessor when it stores in the data memory the voltage values obtained for the black and white standards. Excessive deviations of the analogue voltages from their nominal values lead to an error indication being displayed as described further below.

It will be appreciated that the resolution of the look-up table could be made finer at the cost of more memory addresses or even a computation made according to an equation derived for curve 302, though at a cost of greater complexity in programming. The resolution of 0.5% involving a look-up table of 200 addresses has been found adequate for paper testing.

When measuring a sample, the holder 34 can be conveniently used to hold the sample against the window. If the sample is very thin then possibly the background provided by holder 34 will affect the measurement. This can be avoided by providing the sample as a number of superposed sheets to increase its effective thickness.

A measurement of opacity is made every time the READ button is pressed to actuate switch 144 (FIG. 2) after a calibration has been made to establish the digitised voltages for the set black and set white levels. The opacity is immediately displayed as a percentage on display unit 120. The CPU 200 (FIG. 3) calculates the opacity from $$(V_S - V_B)/(V_W - V_B) \times SV \qquad (1)$$

where $V_S$ is the digitised voltage from the sample being measured and $V_B$ and $V_W$ are the digitised voltages from the black and white standards 38 and 44 respectively, and SV is a secondary value related to the white standard and derived as follows.

The microprocessor program includes a routine executed during the RESET procedure in the instrument whereby it scans through the look-up table to effectively find the value on line 300 in FIG. 4 that corresponds to the ordained corrected value of 78% for the vitrolite tile. This secondary value is 72.0 in the illustrated example. Because the look-up table effectively stores the line 300 in a sequence of equal increments (each accompanied by the corrected value on curve 302) the secondary value can be obtained by scanning the table from 00.0 and counting the number of increments to reach the step corresponding to the corrected 78.0%. The number thus counted is held in the data memory 214 for use in subsequent computations.

Consequently a computation then made according to the above equation yields, after rounding, a secondary value for the measurement being made that is a position in terms of a step number in the look-up table. From this step number in the table the corrected value of the reflectance of the sample is obtained.

The advantage of this procedure is that the microprocessor can use any look-up table compiled in similar fashion whatever the correction curve stored in that table.

As already explained, each individual measurement is the average of a large number of successive measurements made with the aid of DAC 112 thereby effecting substantial filtering.

The instrument is arranged to do more than produce an individual result for each measurement. For testing purposes the program in memory 212 contains routines for calculating the mean of a succession of measurements and the standard deviation of the measurements. Such routines are called up by pressing the COMPUTE C.I. button (the instrument being set in the opacity measurement condition by switch 222).

For performing the above and reading out the results, the data memory 214 can store up to 255 separate opacity measurements. The number of measurements is also counted so that the mean opacity is simply the sum of the measurements to date divided by the number of measurements. This is calculated by the CPU 200. The CPU also calculates the standard deviation which involves the summing of squares. Although the CPU 200 is an eight-bit device, its arithmetic registers could be organized to handle arithmetic of up to sixty-four bits in eight-bit blocks. That facility is used here to deal with the relatively large number of bits required for the squared values and to achieve sufficient computational accuracy.

Upon the COMPUTE C.I. button being pressed, the microprocessor first determines whether there are at least three measurements available. If not, the letters EE appear on display 120. If a succession of measurements is being taken and the counted number reaches 255, the microprocessor causes the display 120 to show the letters DD. At this time either the COMPUTE C.I. button should be pressed to compute on the data so far gathered or the RESET button pressed to clear the data.

Pressing the COMPUTE C.I. button causes the mean percentage value to be shown on display 120. The reading out of the standard deviation requires an auxiliary device such as a printer connected to the port 208 of I/O device 202. To this end, the switch 223 is put to ON, calling up a print-out routine in the program memory 212. This routine causes both mean and standard deviation to be printed.

With the switch 222 set into the compute calender intensity condition, the same operational routines are employed but a different calculation routine is used whose basis will now be explained.

Figure 5:
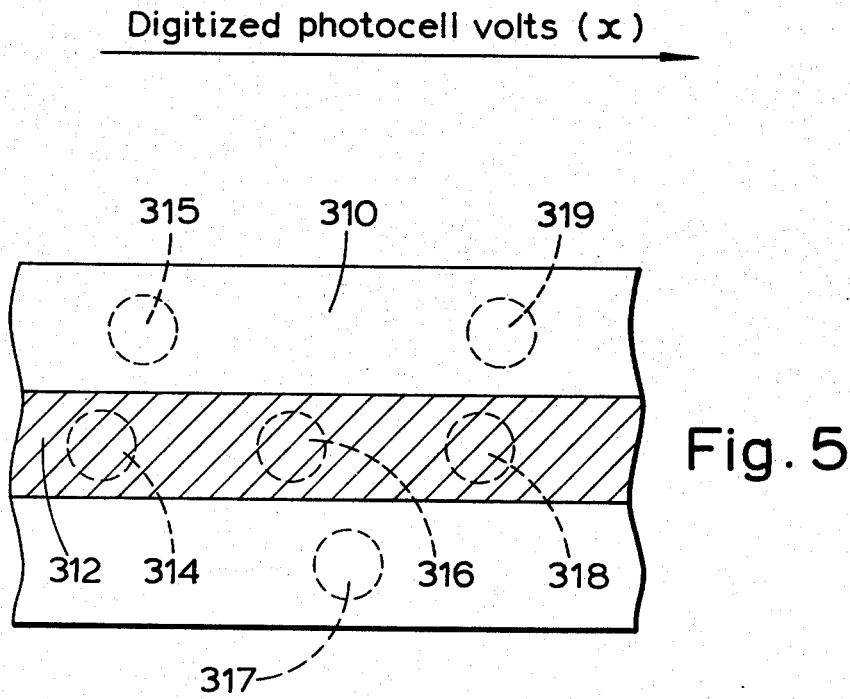
FIG. 5 is a fragmentary view of a sample prepared for calender intensity measurement.

The making of C.I. measurements will be described with reference to FIG. 5, which shows by way of example a strip of carbonless copy paper 310 having a white surface and which has been produced by calendering along a central strip 312 thereof to provide a zone of colour. The clarity with which the central strip 312 is seen against the remainder of the sheet is dependent on the reflectance of the background as well as that of zone 312, i.e. the contrast between the two. Thus the reflectance of a portion 314 of the zone 312 should be compared with an adjacent uncalendered area 315. The strip 310 may be subject to local variations both in background and calender intensity and any meaningful measurement should be taken over a succession of such areas such as 316/317, 318/319 and so on. If the background, i.e. the basic strip, is sufficiently uniform in reflectance, then only one background measurement need be made with switch 227 in its other position.

The calender intensity (C.I.) is expressed as follows $$C.I. = (\overline{M} \times 100\%)/M_b, \quad (2)$$

where $\overline{M}$ is the mean measured reflectance (opacity) taken over at least three areas, and $M_b$ is the background reflectance (opacity) which may be taken from one or more areas. For the purposes of the following description it will be assumed that a single background measurement is taken and this needs to be separated from the other measurements on the zone 312 and stored in the data memory 214 for use as the value $M_b$. To this end, use is made of the SET BACKGROUND indicator 133 controlled by the microprocessor program in the calender intensity mode. To illustrate the interaction between the microprocessor and the operator a complete measurement sequence will now be described.

Step 1—Switch on:

CC (reset complete) is displayed by display 120. The switch on includes the provision of a reset signal corresponding to that from switch 150. The microprocessor also illuminates the SET BLACK indicator 131.

Step 2—Set Black:

The black standard 38 is placed over window 74 by the operator and the READ button 144 pressed. The microprocessor records the digitised voltage from photocell 24 as the black level and display 120 shows 00.0. If the black level is out of limits, the letters AA are displayed. An adjustment of the instrument is then required. Assuming all is well, the microprocessor then causes the SET WHITE indicator 132 to be lit.

Step 3—Set White:

The white standard 44 is placed over window 14 by the operator and the READ button pressed. The microprocessor records the digitised voltage for white level and the reflectance value 78.0 for the white level is shown on display 120. If the white level is out of limits the display shows the letters AB, indicating an instrument adjustment is needed. Assuming all is well, the microprocessor now illuminates the SET BACKGROUND indicator 133.

Step 4—Set Background:

If the background value measured in a preceding measurement sequence is still required, then operating the COMPUTE C.I. switch 146 causes the display 120 to indicate that value, the opacity indicator 134 to be illuminated, and the microprocessor proceeds with step 5. If there is no value, or if the operator wishes to remeasure, then the operator places a background area, e.g. 315, of the sample 310 over the window and presses the READ button 144. The microprocessor computes the opacity of the sample area, saves the value in data memory 214, and displays the value on unit 120. The opacity indicator 134 is now illuminated and the microprocessor proceeds to step 5.

If the instrument is in the mean background mode, a series of measurements may be made on sample 310 say at 315, 317 and 319. A minimum of 3 measurements must be made. Each measurement is made by operating the READ button. Display 120 indicates opacity after every operation of the READ button. To terminate this sequence, the COMPUTE C.I. button is operated. This causes the microprocessor to compute and display on 120 the mean value. This value is saved in data memory 214 and used later to compute C.I. If a printer is connected the mean and standard deviation will be provided. On completion, the opacity indicator 134 will be illuminated.

Step 5—Opacity measurement:

The operator places the sample over the window 14 at a calendered area, e.g. 314, and presses the READ button. Again, the microprocessor computes and displays the opacity of that area. The OPACITY indicator remains illuminated and a succession of measurements, e.g. areas 316, 318, and so on, can be taken up to a total of 255.

Step 6—Compute C.I.

When the operator has as many measurements as wanted, the COMPUTE C.I. switch 146 is pressed and the C.I. value computed and displayed. If in fact less than three opacity measurements have been taken in Step 5, then the letters EE are displayed and the OPACITY indicator remains illuminated, enabling further opacity measurements to be made. Upon completion of the C.I. step, the SET BACKGROUND indicator 133 is illuminated so that the sequence of Steps 4, 5 and 6 can be repeated for different samples, the original SET BLACK and and SET WHITE levels being retained.

In order to re-set the black and white levels, the RESET button 150 is pressed to put the instrument back to Step 1. The steps listed above will include appropriate print-out operations or transmission to other apparatus where this condition has been set up.

The checking of calibration can be made at any time by placing either the black or white standard in holder 34 over window 14 or the magnesium block. The CHECK CALIBRATION switch 145 is pressed and the digitised voltage recorded in the data memory 214. The memory stores the nominal values corresponding to these standards and compares the value read in with the stored values to ascertain whether it falls within the limits prescribed for any one of the nominal values. If so, then the display unit 121, 122 shows CA, calibration correct. If the value read in does not correspond to any nominal value, the display shows BB and the instrument is set into the SET BLACK mode. The instrument then has to be recalibrated. If, after recalibration the magnesium carbonate block fails either to indicate a value of 98.0% or if in the check calibration mode a response of CA, then the instrument needs an internal adjustment.

When the RESET button is pressed or upon switching on, all the registers in the CPU 200, the data memory 214 and the I/O ports are cleared. However, if any data remain to be printed out this is cleared first.

When the instrument is set to perform opacity measurement only, Step 4—Set Background is omitted, the sequence going straight to Step 5 with the microprocessor illuminating the OPACITY indicator 134. In this case, the pressing of the COMPUTE C.I. button in Step 6 causes the mean opacity to be calculated and displayed. Again, a minimum of three measurements is required.

The foregoing description sets out the nature of the measurements made, how calibration is achieved and results are calculated, and how the microprocessor program routines are performed and their interaction with the operator. FIGS. 6 A to I show individual routines in rather more detal in the form of flow diagrams. To complement the brief legends appearing on the flow diagrams, the routines are set out in greater detail below, the steps being numbered in accord with the reference numerals on the flow diagrams.

ROUTINE 1: START UP OR RESET (FIG. 6A)

Accessed after the instrument is switched on, or when the reset switch is operated.

| STEP | |
|---|---|
| 601 | Has the instrument already been in use? |
| 602 | Any stored C.I. or average opacity data? |
| 603 | Compute Mean, and Standard Deviation for this data. |
| 604 | Is a printout required? |
| 605 | Print "Mean" and computed result. |
| 606 | Print "Standard deviation" and computed result. |
| 607 | Zero all registers, memory for data, and I/O Ports. |
| 608 | Note the instrument is now ready for operation. |
| 609 | Go to ROUTINE 2. |

Figure 6A:
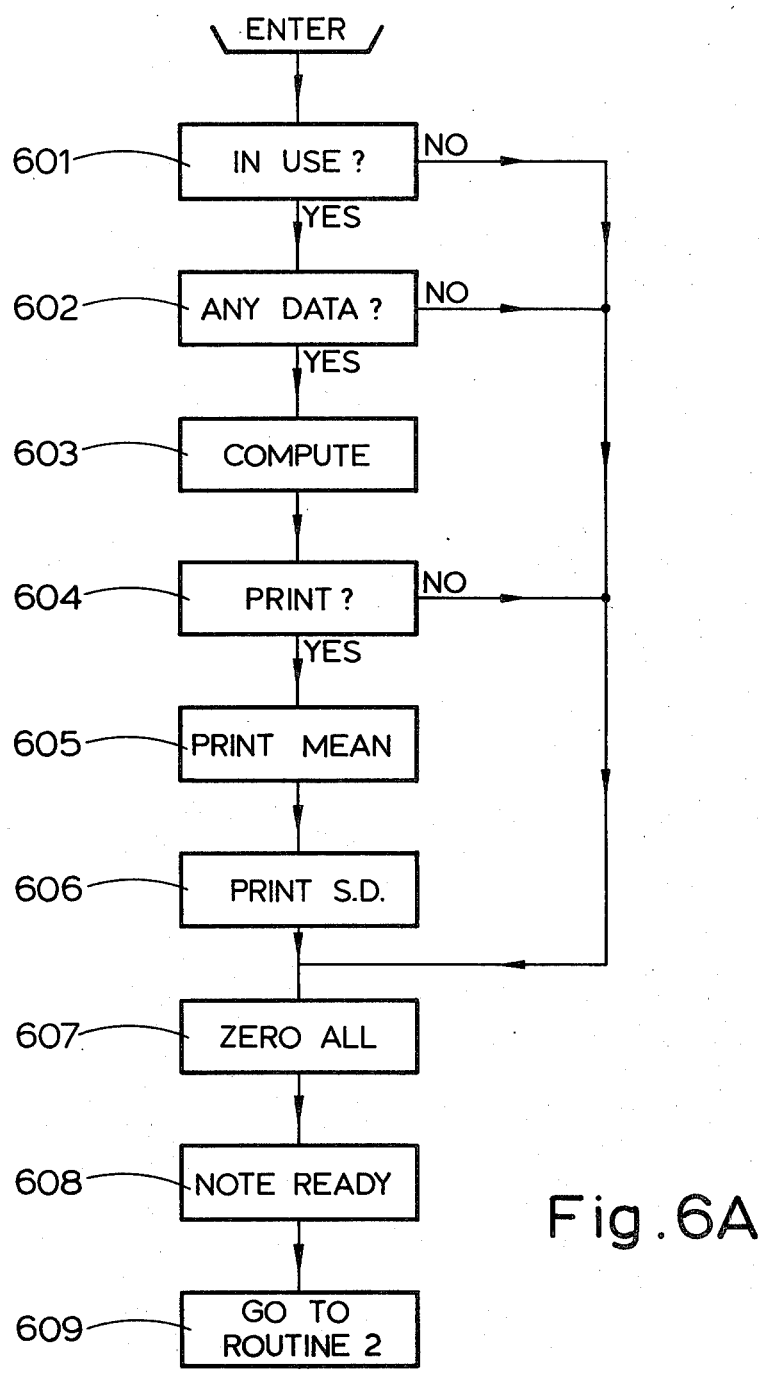
FIGS. 6 A-I are flow diagrams of routines performed by the microprocessor system.
Figure 6B:
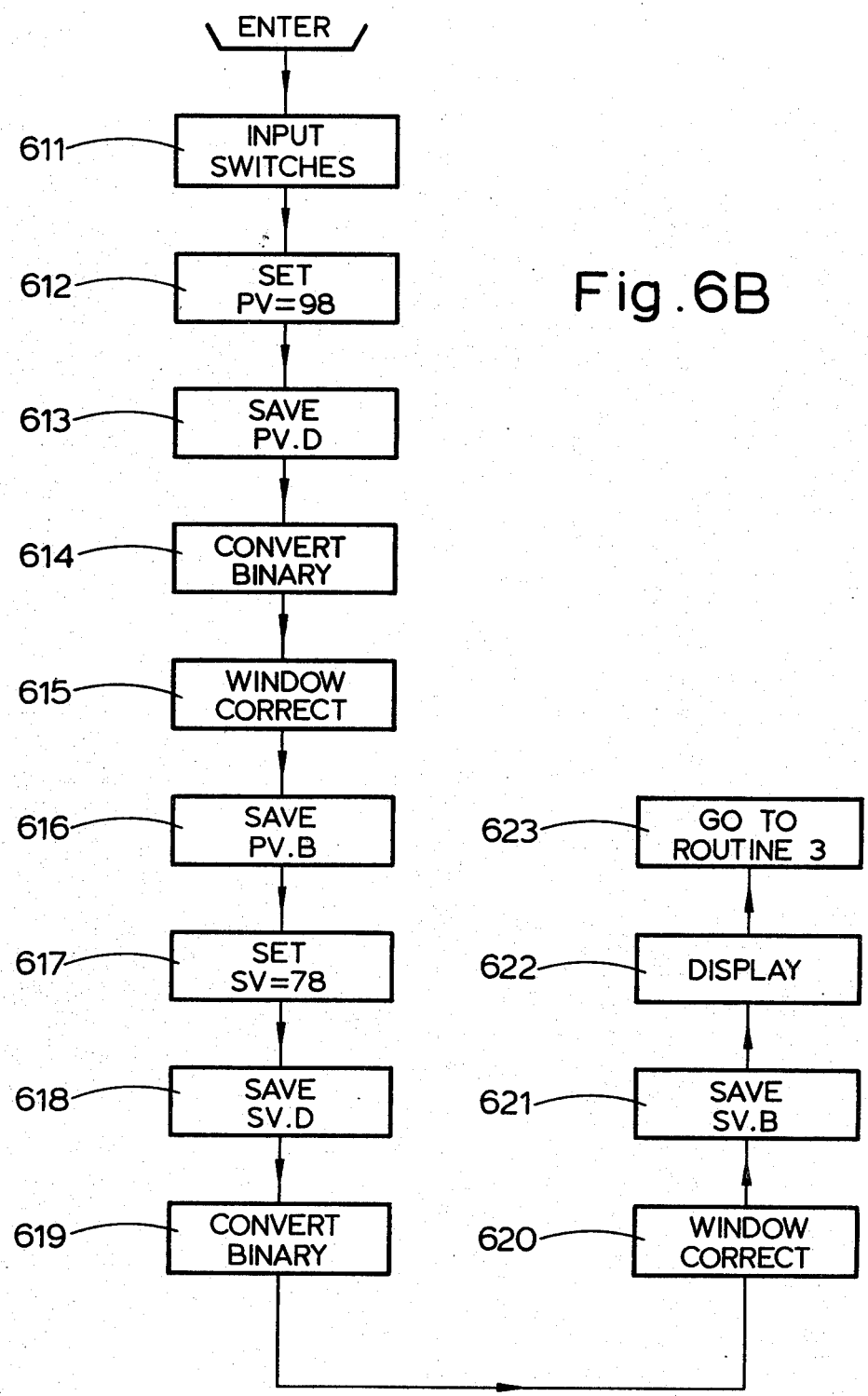
Figure 6C:
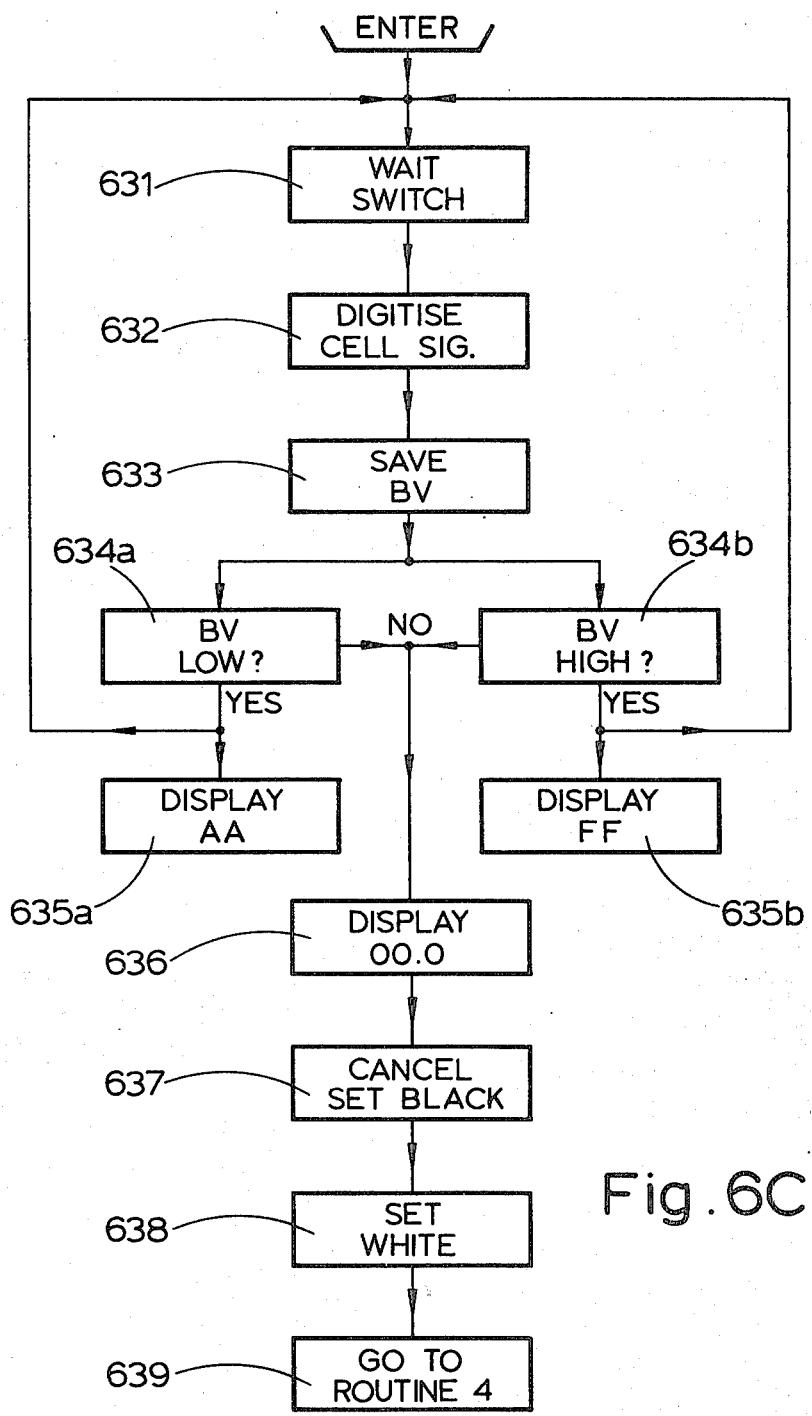
Figure 6D:
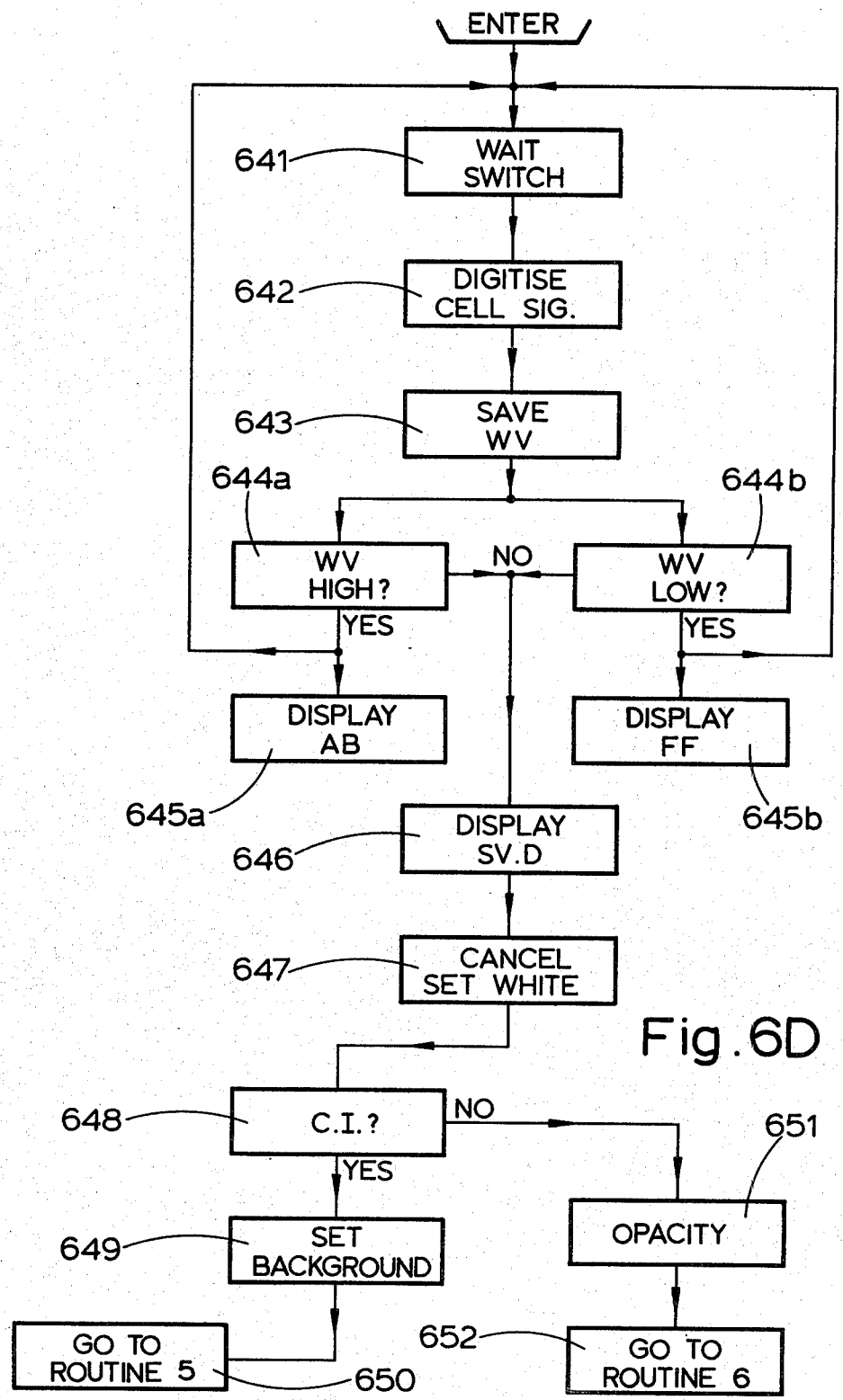
Figure 6E:
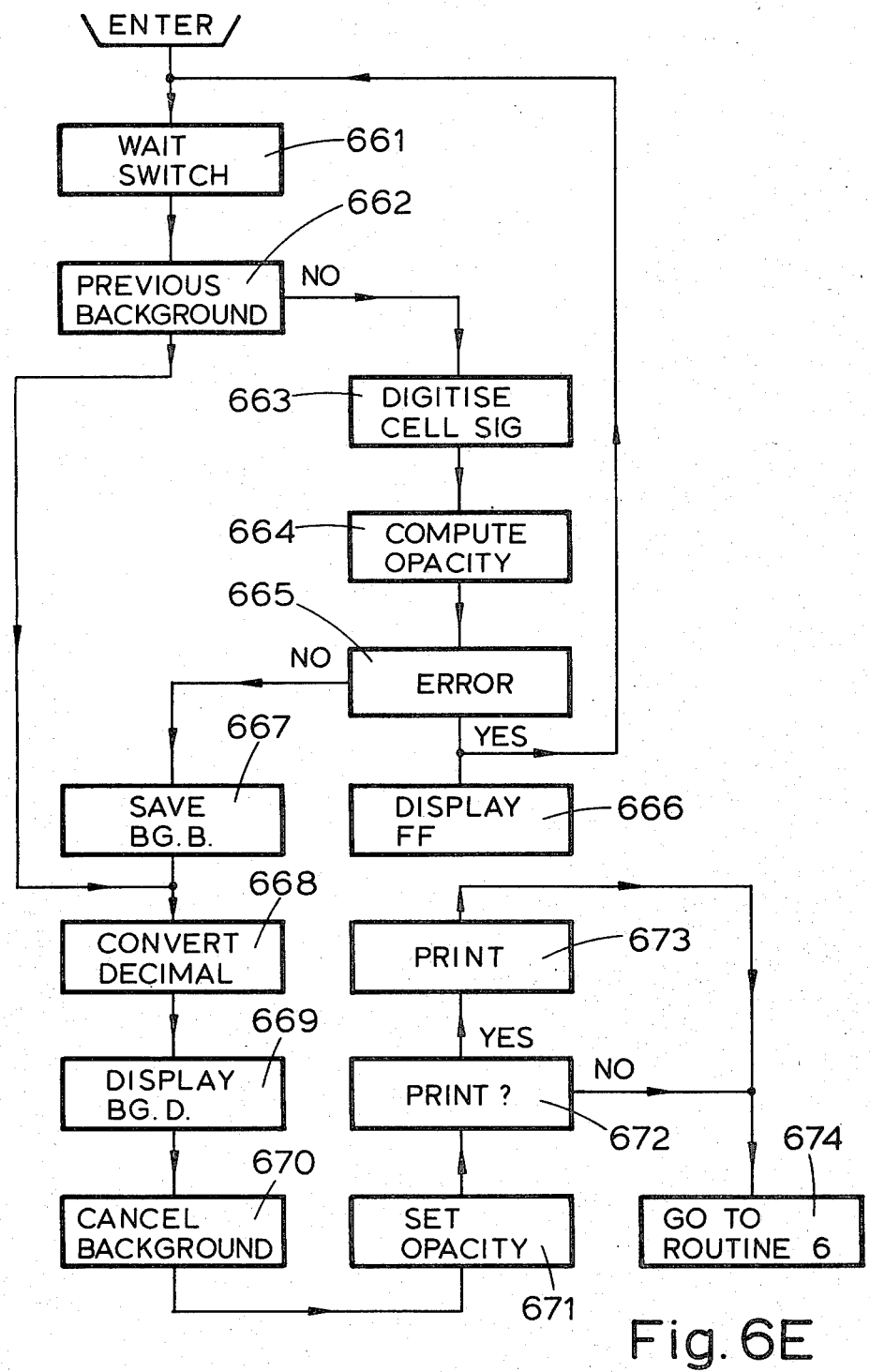
Figure 6F:
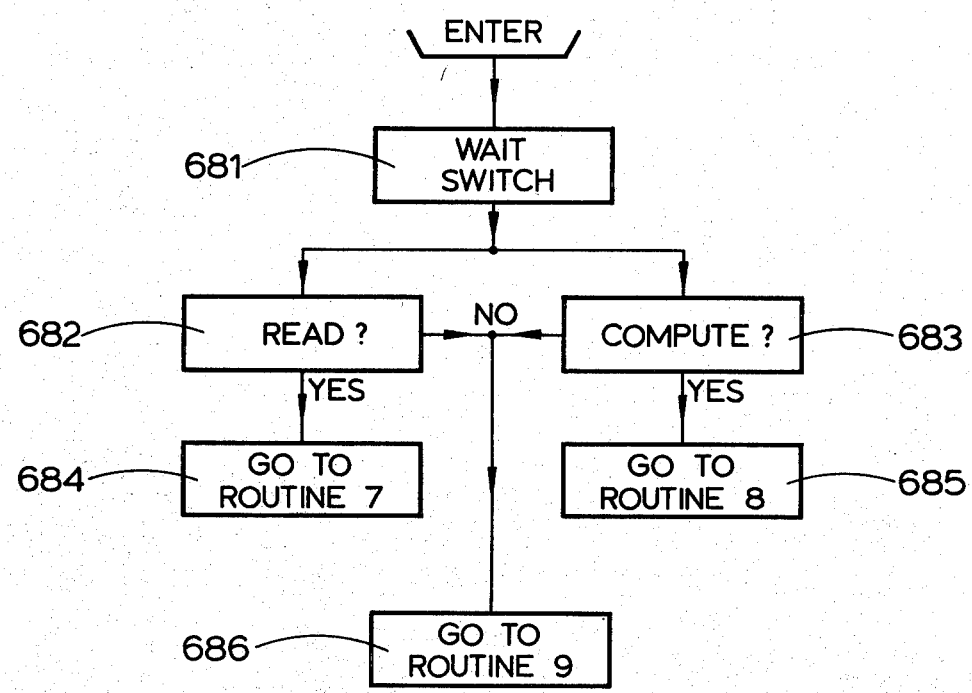
Figure 6G:
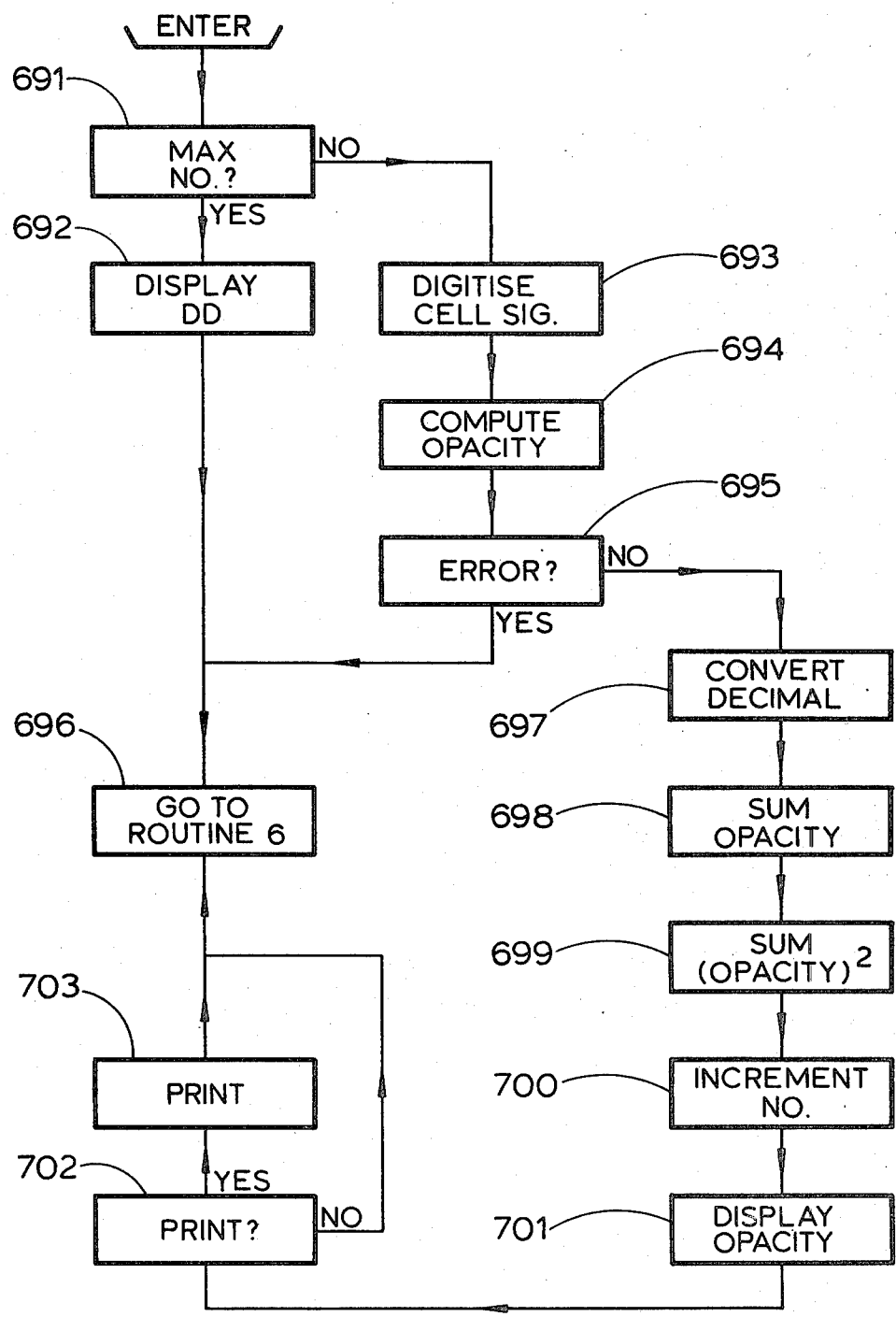
Figure 6H:
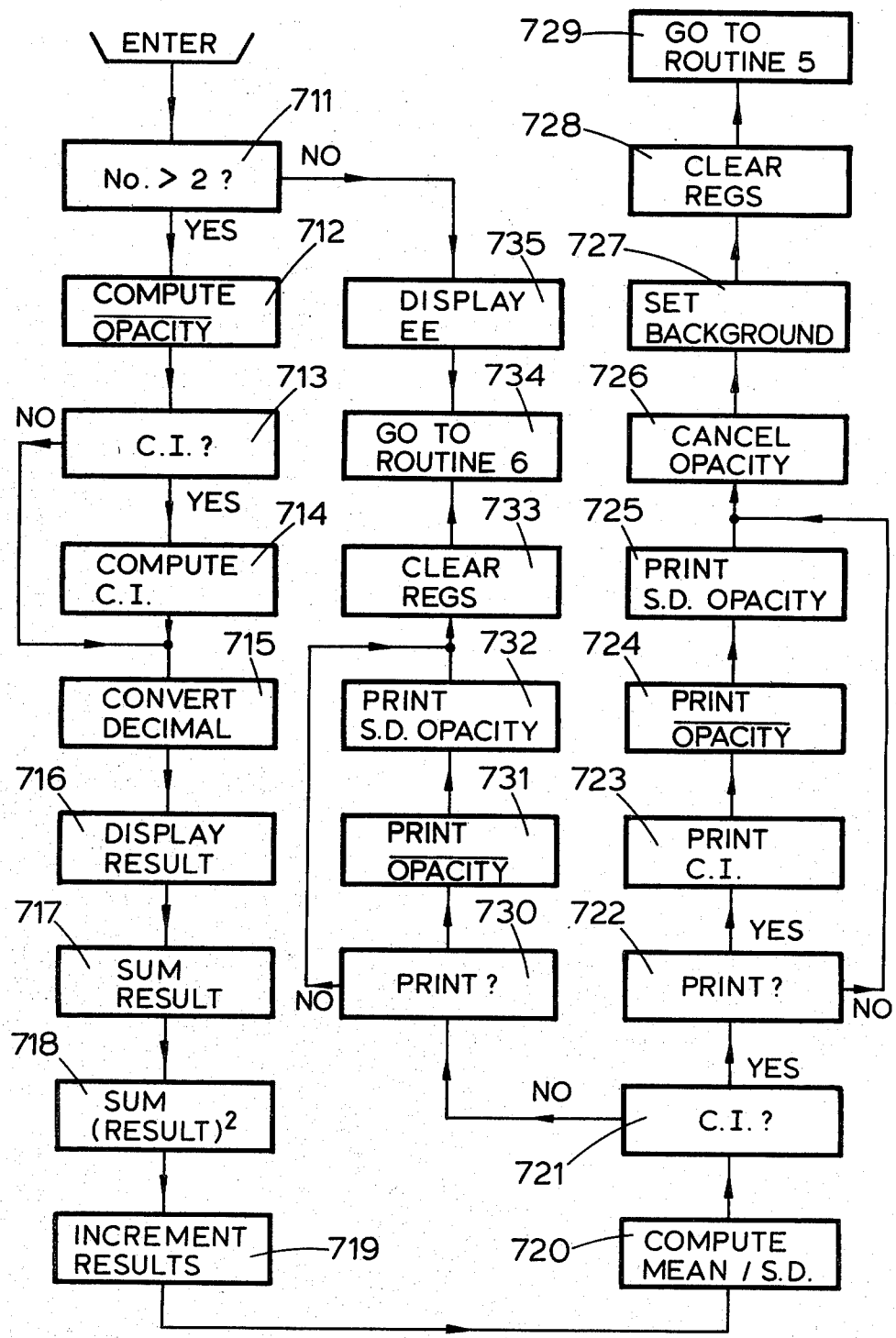
Figure 6I:
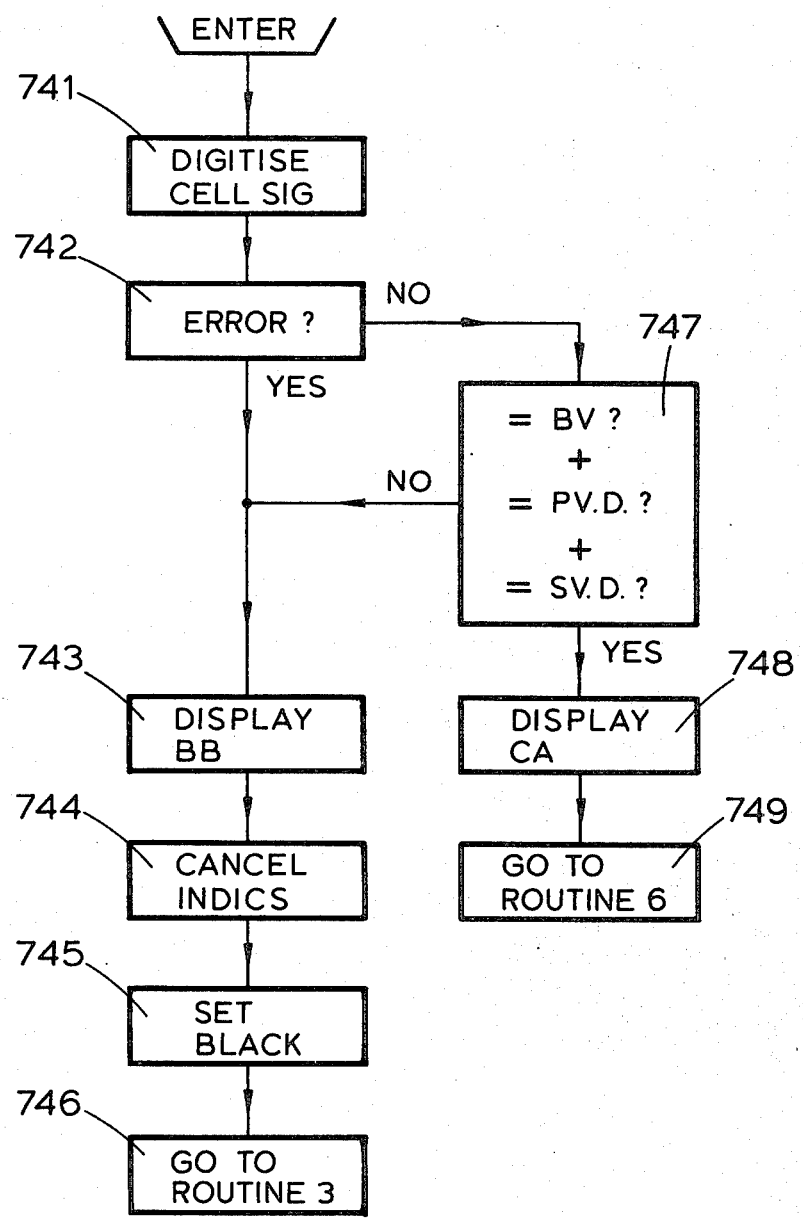

ROUTINE 2: INPUT DIGIT SWITCH DATA, SET DISPLAY TO CC, AND SWITCH ON "SET BLACK" INDICATOR (FIG. 6B)

| STEP | |
|---|---|
| 611 | Input dual in line switch (220 in FIG. 3) information and remember settings. |
| 612 | Set primary white value (PV) to 98. |
| 613 | Save primary value in Register in decimal form (PV.D). |
| 614 | Convert primary decimal value to binary. |
| 615 | Correct the binary value for window effect. |
| 616 | Save corrected primary value in Register in binary form (PV.B). |
| 617 | Set secondary white value to 78. |
| 618 | Save secondary value in Register in decimal form (SV.D). |
| 619 | Convert secondary decimal value to binary. |
| 620 | Correct the binary value for window effect. |
| 621 | Save corrected secondary value in Register in binary form (PV.B). |
| 622 | Display "CC" (reset complete) and switch on "Set Black" indicator. |
| 623 | Go to ROUTINE 3 (Set Black). |

In this routine the primary white value relates to a primary white standard such as a Magnesium Carbonate block. The secondary white value relates to the instrument's built-in standard (44 in FIG. 1), i.e. the vitrolite tile described.

ROUTINE 3: SET BLACK (FIG. 6C)

| STEP | |
|---|---|
| 631 | Wait for a switch to be operated, e.g. READ switch 144, FIG. 2. |
| 632 | In response to switch operation, digitise the current analogue signal from photocell amplifier 108. |
| 633 | Save this digitised black value (BV) in Register. |
| 634a,634b 635a,635b | Examine BV to ascertain<br>(a) if it lies below the allowed minimum (0.1 volt in the example quoted) for the black value in which case the display is set to AA-black level low; or |

| STEP | |
|---|---|
| | (b) if it exceeds 25% of the allowed maximum of the photocell output signal in which case display is set to FF-error. |
| 636 | If BV lies within the limits, set display to 00.0. |
| 637 | Switch off SET BLACK indicator. |
| 638 | Switch on SET WHITE indicator. |
| 639 | Go to ROUTINE 4 (SET WHITE). |

ROUTINE 4: SET WHITE (FIG. 6D)

| STEP | |
|---|---|
| 641 | Wait for a switch to be operated, e.g. READ switch 144. |
| 642 | In response to switch operation, digitise the current analogue signal from photocell amplifier 108. |
| 643 | Save this digital white value (WV) in Register. |
| 644a,644b 645a,645b | Examine BV to ascertain: (a) if it lies at the maximum allowable voltage in which case the display is set to AB-white level high; or (b) if it lies below 50% of the maximum allowable voltage in which case the display is set to FF-error. |
| 646 | If WV lies within the limits, set display to SV.D (see ROUTINE 2 - step 618). |
| 647 | Switch off SET WHITE indicator. |
| 648 | Is the instrument set up to C.I. measurement? |
| 649 | If C.I. measurement required, switch on SET BACKGROUND indicator. |
| 650 | Go to Routine 5 (SET BACKGROUND). |
| 651 | If C.I. measurement not required, switch on OPACITY indicator. |
| 652 | Go to ROUTINE 6 (SELECT FUNCTION). |

ROUTINE 5: SET BACKGROUND (FIG. 6E)

| STEP | |
|---|---|
| 661 | Wait for a switch to be operated, e.g. switch 144. |
| 662 | Is a previously acquired Background value still required? |
| 663 | If a fresh Background value is required, digitise the signal from photocell amplifier 108. |
| 664 | Compute the opacity value from the digitised value. |
| 665,666 | If opacity value is invalid, display FF-error. |
| 667 | If opacity value is valid, save the opacity value in binary (BG.B) in Register. |
| 668 | Convert BG.B value to decimal (BG.D). |
| 669 | Display BG.D. |
| 670 | Switch off SET BACKGROUND indicator. |
| 671 | Switch on OPACITY indicator. |
| 672 | Is printout of Background result required? |
| 673 | If printout required, print "Background" and result (BG.D). |
| 674 | Go to ROUTINE 6 (SELECT FUNCTION). |

ROUTINE 6: SELECT FUNCTION (FIG. 6F)

| STEP | |
|---|---|
| 681 | Wait for a switch to be operated, i.e. switch 144, 145 or 146. |
| 682,683 | Was READ switch 144 or COMPUTE C.I. switch 146 operated? |
| 684 | If READ switch operated, go to ROUTINE 7 (MEASURE OPACITY). |
| 685 | If COMPUTE C.I. switch operated, go to ROUTINE 8 (COMPUTE). |
| 686 | If neither READ nor COMPUTE C.I. switches operated, then CHECK CALIBRATION switch 145 operated and go to ROUTINE 9 (CHECK CALIBRATION). |

ROUTINE 7: MEASURE OPACITY (FIG. 6G)

| STEP | |
|---|---|
| 691 | Has the maximum number (256) of measurements allowed been reached? |
| 692 | Display DD - no more measurements, compute C.I. or reset. |
| 693 | Digitise the output of the photocell amplifier 108. |
| 694 | Compute opacity from the digitised value. |
| 695 | Is the computed opacity value valid? |
| 696 | Go to ROUTINE 6 (SELECT FUNCTION). |
| 697 | Convert the computed opacity value to decimal form. |
| 698 | Add the opacity value to the existing opacity sum value. |
| 699 | Add the square of the opacity value to the existing opacity squared sum value. |
| 700 | Increment the number of measurements made by one. |
| 701 | Display the opacity value. |
| 702 | Is printout of opacity value required? |
| 703 | Print opacity value. |

ROUTINE 8: COMPUTE (FIG. 6H)

| STEP | |
|---|---|
| 711 | Are there sufficient measurements, 3 or more in case exemplified? |
| 712 | Sufficient measurements: compute mean opacity for number taken. |
| 713 | Is C.I. mode operative? |
| 714 | If in C.I. mode, compute C.I. from mean opacity and background values. |
| 715 | Convert the mean opacity or C.I. value, as the case may be, to decimal form. |
| 716 | Display the decimal value. |
| 717 | Add this value to the sum of the preceding values. |
| 718 | Add the square of the value to the sum of the preceding squared values. |
| 719 | Increment existing number of summed values by one. |
| 720 | Compute mean and standard deviation of the opacity value. |
| 721 | Is C.I. mode operative? |
| 722 | Is printout of C.I. results required? |
| 723 | Print "C.I.=" and value. |
| 724 | Print "Mean Opacity=" and value |
| 725 | Print "Standard Deviation=" and value |
| 726 | Switch off OPACITY indicator. |
| 727 | Switch on SET BACKGROUND indicator. |
| 728 | Clear operating Registers. |
| 729 | Go to ROUTINE 5 (SET BACKGROUND). |
| 730 | Is printout of opacity results required? |
| 731 | Print "Mean Opacity=" and value. |
| 732 | Print "Standard Deviation=" and value. |
| 733 | Clear operating Registers. |
| 734 | Go to ROUTINE 6 (SELECT FUNCTION) |
| 735 | Display EE - Insufficient data to compute mean opacity/C.I. |

ROUTINE 9: CHECK CALIBRATION (FIG. 6I)

| STEP | |
|---|---|
| 741 | Digitise the analogue photocell signal at the output of amplifier 108. |

| STEP | -continued |
|---|---|
| 742 | Is the digitised value valid? |
| 743 | Display BB - calibration error, recalibrate - for an invalid value. |
| 744 | Switch off any illuminated indicators. |
| 745 | Switch on SET BLACK indicator. |
| 746 | Go to ROUTINE 3, SET BLACK. |
| 747 | Is the digitised value equal to any one of the established values BV, PV.D or SV.D? |
| 748 | If equality found with any one of the established values, display CA - calibration correct. |
| 749 | Go to ROUTINE 6 (SELECT FUNCTION). |

In this routine the values PV.D and SV.D are the values of primary white and secondary white in decimal form stored in ROUTINE 2. The value BV is the digitised black value obtained in ROUTINE 3.

Consideration will now be given to the measurement of opacity (TAPPI). We are here concerned with the actual measurement steps rather than the construction of the apparaus, for example the construction of the optical system discussed above.

The apparatus described can be used in accord with TAPPI standards by adapting steps of the C.I. measurement to opacity measurement, and by adding an additional calculational routine assuming the WHITE standard is the 78% reflectance vitrolite tile. To measure opacity (TAPPI), the apparatus is put into the C.I. mode and the following measurement sequence is performed.

1. Switch on: CC displayed and the SET BLACK indicator illuminated (as before)
2. Set zero: place BLACK standard over the measurement window and press the READ switch. Zero (00.0) is displayed and the SET WHITE indicator illuminated.
3. Set white: place WHITE standard over the measurement window and press READ switch. The reflectance value (78.0) for the white standard is displayed and the SET BACKGROUND indicator is illuminated. For the present measurements, this step becomes BACKGROUND WHITE.
4. Background white: place paper sample over the measurement window backed by the WHITE standard and press READ switch. The reflectance value (white) for the sample will be displayed (this step may be repeated for an average measurement if desired as described in the C.I. measurement method). The OPACITY indicator will now be illuminated. For the present measurements, this step becomes BACKGROUND BLACK.
5. Background black: place the same paper sample over the measurement window backed by the BLACK standard and press READ switch. The reflectance value (black) will be displayed and the OPACITY indicator remains illuminated. Repeat this step to take more measurements, that is at least three as described for C.I. measurement (the making of multiple measurements is not a TAPPI standard requirement).
6. Compute Opacity: press COMPUTE C.I. switch and the opacity (TAPPI) value is displayed.

In computing opacity by step 6, the microprocessor performs the computation of equation (2), but in this case the values $\overline{M}$ and $M_b$ are replaced by the values $R_w$ and $R_b$ representing the reflectance value (white) and reflectance value (black) of steps 4 and 5 above.

The value thus obtained is referred to the 78% reflectance WHITE standard. The TAPPI standards call for an 89% reflectance standard (TAPPI standard A 6.4). If such a standard is substituted for the vitrolite tile and the instrument adjusted accordingly to this value as the white reference, then the computation according to equation (2) using $R_w$ and $R_b$ will directly give the opacity (TAPPI). An alternative is to continue using the 78% reflectance standard and to correct the above computed value to a value appropriate to the 89% reflectance standard. Such correction can be made in accord with the known Kulbelka-Munk theory. The correction thus becomes an additional computational sub-routine called up when opacity (TAPPI) is required.

For an instrument intended for opacity (TAPPI) rather than C.I. measurement, the C.I. legends can be replaced where necessary by the legends at the left of the above list of steps, or supplemented by such legends where the instrument is capable of performing in both modes.

The TAPPI standard also calls for a resolution of 0.1%. The instrument that has been described provides a resolution to 0.5% which is considered adequate. The instrument is capable of the higher resolution since the conversion procedure performed with the aid of DAC 112 (FIG. 2) is to 10 bits, i.e. a potential resolution of 1 part in 1024, and the 0.5% resolution described is produced by rounding off. By exploiting this existing potential and using an enlarged look-up table—1000 as against 200 places—a read out to 0.1% may be achieved.

The enlarged look-up table can be permanently stored in a memory of greater capacity. Alternatively, as already mentioned, the reflectance values could be calculated every time from a knowledge of the curve of FIG. 4 or the curve could be stored as a polynomial equation from which the required look-up table is generated for storage in a volatile memory as a sub-routine upon switching on the instrument. Each instrument would then only differ from others by having memory space set aside in which is stored its particular polynomial equation.

What is claimed is:

1. Apparatus for measuring the opacity of a sample area comprising:
   an enclosure having a radiation transmissive window defining a station for receiving a sample to be measured;
   means within said enclosure for directing radiation through the window at said station and photo-electric means within said enclosure for receiving such radiation reflected through the window from a sample placed at said station;
   first and second defined standards of reflectance locatable in said station;
   said window exhibiting a non-linear effect on the intensity of the radiation transmitted to said photoelectric means as a function of the reflectance of the sample located at said station;
   a circuit arrangement connected to said photo-electric means to process electrical signals obtained therefrom in response to the location of said standards and a sample to be measured at said station, said circuit arrangement including a microprocessor system and being operable to digitize said electrical signals for use by the microprocessor system, and wherein said microprocessor system includes means storing program routines for enabling the microprocessor system to compute, from a digitized signal obtained from a sample, a value representing the apparent reflectance of said sample with reference to the digitized signals obtained from said standards, such apparent reflectance values having a non-linear relationship to the true reflectance values of samples over a measured range of reflectance;

means storing information defining said non-linear relationship; and said stored program routines controlling the microprocessor system to derive the true reflectance of a sample from the computed apparent reflectance value with the aid of the stored non-linear relationship information.

2. Apparatus as claimed in claim 1 in which said storage means stores said non-linear relationship information as a step-wise look-up table, and said microprocessor system is controlled by said program routines to perform a rounding operation to provide said apparent reflectance values in a corresponding step-wise fashion.

3. Apparatus as claimed in claim 2, in which said microprocessor system is operable to sum a series of computed reflectance values and to count the number of values summed in order to determine an average value for the series therefrom.

4. Apparatus as claimed in claim 1 in which said non-linear relationship information is stored in the form of a polynomial equation for computing true reflectance values from apparent reflectance values.

5. Apparatus as claimed in claim 1 in which said circuit arrangement further includes a digital-to-analog converter (DAC) having its digit inputs connected to the microprocessor system for selective activation thereby and a comparator having a first input connected to the analog output of the DAC, a second input connected to receive the electrical signal derived by said photo-sensitive means, and an output coupled to the microprocessor system whereby under the control of a program routine, the microprocessor system is operable to monitor the comparator output and establish a digital value at the DAC input equivalent to the electrical signal at the second input of said comparator, the microprocessor system further including means for storing such digital values for use in computation.

6. The apparatus of claim 1 wherein said microprocessor system includes means for computing the reflectance of a first sample with reference to the reflectance values of said standards and for computing the reflectance of a second sample with reference to the reflectance values of said standards, means for storing the two computed reflectance values, and means for computing the reflectance of the first sample as a percentage of that of the second sample on the basis of said stored values.

7. Apparatus as claimed in claim 6 in which the source of radiation provides white light and further comprising filter means in the path between said source and said photo-electric means that provides a response approximating that of the human eye.

8. Apparatus as claimed in claim 1, 6 or 7 in which said window is of saphire.

9. Apparatus as claimed in claim 1, 6 or 7 in which said source provides collimated light and said window is of sapphire.

10. In an apparatus for measuring the opacity of a sample area comprising:

an enclosure having a radiation transmissive window defining a station for receiving a sample to be measured;

means within said enclosure for directing radiation through the window at said station and photo-electric means within said enclosure for receiving such radiation reflected through the window from a sample placed at said station;

first and second defined standards of reflectance locatable at said station;

said window exhibiting a non-linear effect on the intensity of the radiation transmitted to said photo-electric means as a function of the reflectance of the sample located at said station;

a circuit arrangement connected to said photo-electric means to process electrical signals obtained therefrom in response to the location of said standards and a sample to be measured at said station, said circuit arrangement including a microprocessor system and being operable to digitize said electrical signals for use by the microprocessor system, and wherein said microprocessor system includes means storing program routines for enabling the microprocessor system to compute, from a digitized signal obtained from a sample, a value representing the apparent reflectance of said sample with reference to the digitized signals obtained from said standards, such apparent reflectance values having a non-linear relationship to the true reflectance values of samples over a measured range of reflectance;

means storing information defining said non-linear relationship; and said stored program routines controlling the microprocessor system to derive the true relectance of a sample from the computed apparent reflectance value with the aid of the stored non-linear relationship information;

the method of measuring the contrast of images produced by a carbonless copy paper formset, the back surface of a first sheet of said formset having a coating of microcapsules containing a solution of color precursors for reacting with the co-reactant on contacting the front surface of a second sheet, comprising the steps of:

(a) applying pressure to a portion of said formset to rupture the microcapsules thereat to provide a colored zone on the second sheet;

(b) measuring the reflectance of at least one first sample area in said zone with said apparatus;

(c) measuring the reflectance of at least on second sample area of said second sheet outside said zone with said apparatus; and (d) computing the reflecting of the first sample area as a percentage of that of the second sample area.

11. The method of claim 10 comprising the steps of measuring the reflectance of a plurality of first sample areas in said zone, and using the average of the measured reflectances to perform the computation of step (d).

12. The method of claim 10 or 11 comprising the steps of measuring the reflectance of a plurality of second sample areas outside said zone, and using the average of the measured reflectances to perform the computaton of step (d).

13. Apparatus for measuring the opacity of a sample area comprising:

an enclosure having a radiation transmissive window defining a station for receiving a sample to be measured;

means within said enclosure for directing radiation through the window at said station and photo-electric means within said enclosure for receiving such radiation reflected through the window from a sample placed at said station;

first and second defined standards of reflectance locatable at said station;

said window exhibiting a non-linear effect on the intensity of the radiation transmitted to said photo-electric means as a function of the reflectance of the sample located at said station;

a circuit arrangement connected to said photo-electric means to process electrical signals obtained therefrom in response to the location of said standards and a sample to be measured at said station, said circuit arrangement including a microprocessor system and being operable to digitise said electrical signals for use by the microprocessor system, and wherein said microprocessor system includes means storing program routines for enabling the microprocessor system to compute a value of reflectance of a sample with reference to the reflectance values of said standards;

means storing information defining the non-linear effect of at least the window on reflectance, said information being stored in the form of a table having a first listing in discrete steps representing increments of apparent reflectance and second listing of true reflectance values in one-for-one correspondence with those of the first listing; and wherein said program routines control the microprocessor to perform an apparent reflection computation according to the equation $$(V_s - V_1)/(V_2 - V_1) \times SV,$$

where $V_s$, $V_1$ and $V_2$ represent the values of digitised electrical signals obtained from a sample, the first standard and the second standard respectively, and SV is a value in the first listing that corresponds to a predetermined reflectance value accorded to said second standard as found in the second listing, and wherein after rounding the computation value obtained by use of said equation to a step in the first listing, the microprocessor system outputs the true reflectance value corresponding in the second listing.

14. Apparatus as claimed in claim 13 in which the microprocessor system is controlled by said program routines to initially acquire the value SV by counting the number of steps upward in the first listing that are required to reach said predetermined reflectance value in the second listing.

15. Apparatus as claimed in claim 14 in which said first standard provides a standard black level, and said second standard provides an adjustable white level, said second standard comprising a holder locatable in a predetermined position at said station and means providing a white standard surface movably mounted in said holder to have its position with respect to the window adjusted whereby its reflectance is settable to a predetermined value.

16. Apparatus for measuring the opacity of a sample area comprising:

an enclosure having a radiation transmissive window defining a station for receiving a sample to be measured;

means within said enclosure for directing radiation through the window at said station and photo-electric means within said enclosure for receiving such radiation reflected through the window from a sample placed at said station;

a. first standard providing a standard black level, and a second standard providing an adjustable white level, said second standard comprising a holder locatable in a predetermined position at said station and means providing a white standard surface movably mounted in said holder to have its position with respect to the window adjusted whereby its reflectance is settable to a predetermined value;

said window exhibiting a non-linear effect on the intensity of the radiation transmitted to said photo-electric means as a function of the reflectance of the sample located at said station;

a circuit arrangement connected to said photoelectric means to process electrical signals obtained therefrom in response to the location of said standards and a sample to be measured at said station, said circuit arrangement including a microprocessor system and being operable to digitise said electrical signals for use by the microprocessor system, and wherein said microprocessor system includes means storing program routines for enabling the microprocessor system to compute the reflectance of a sample with reference to the reflectance values of said standards;

means storing information defining the non-linear effect of at least the window on reflectance; and said stored program routines controlling the microprocessor system to derive a value of true reflectance of a sample with the aid of the stored non-linearity information.

17. Apparatus as claimed in claim 4, 16, or 15 in which said circuit arrangement comprises an operational amplifier circuit to which said photo-electric device is connected to obtain a light-dependent analog voltage for digitization, said operational amplifier circuit including first and second pre-settable circuit elements for setting the gain and offset voltage of the operational amplifier circuit to obtain predetermined analog voltages corresponding to the location of said first, black, standard and a magnesium carbonate block at said station, and wherein said means providing said white standard surface has its position adjusted to provide a predetermined value of said analog voltage with the pre-set values of said circuit elements.

18. Apparatus as claimed in claim 16 or 34 in which said circuit arrangement comprises an operational amplifier to which said photo-sensitive device is connected to obtain a light-dependent analog voltage for digitisation, and an operational amplifier circuit including first and second pre-settable circuit elements for setting the gain and offset voltage of the operational amplifier circuit to obtain predetermined values of true reflectance of 0% and 98% corresponding to the location of said black standard and a magnesium carbonate block at said window, and wherein said white standard surface has its position adjusted to provide a predetermined value of said analog voltage with the pre-set values of said circuit elements.

* * * * *